(12) United States Patent
Cohen et al.

(10) Patent No.: US 9,199,755 B1
(45) Date of Patent: Dec. 1, 2015

(54) APPARATUS AND METHODS FOR HANDLING TUBES OR VIALS

(71) Applicants: Joseph Cohen, Encinitas, CA (US); Jonathan David Dambman, San Diego, CA (US); Jeffrey Lee Martin, San Diego, CA (US); Thomas Herbert Gilman, San Diego, CA (US)

(72) Inventors: Joseph Cohen, Encinitas, CA (US); Jonathan David Dambman, San Diego, CA (US); Jeffrey Lee Martin, San Diego, CA (US); Thomas Herbert Gilman, San Diego, CA (US)

( * ) Notice: Subject to any disclaimer, the term of this patent is extended or adjusted under 35 U.S.C. 154(b) by 484 days.

(21) Appl. No.: 13/763,674

(22) Filed: Feb. 9, 2013

Related U.S. Application Data

(60) Provisional application No. 61/597,765, filed on Feb. 11, 2012.

(51) Int. Cl.
| | |
|---|---|
| *B65B 69/00* | (2006.01) |
| *B67B 7/02* | (2006.01) |
| *B67B 7/18* | (2006.01) |
| *A47B 81/00* | (2006.01) |
| *A47B 73/00* | (2006.01) |
| *B01L 9/06* | (2006.01) |

(52) U.S. Cl.
CPC ................. *B65B 69/00* (2013.01); *A47B 73/00* (2013.01); *A47B 81/007* (2013.01); *B01L 9/06* (2013.01); *B67B 7/02* (2013.01); *B67B 7/182* (2013.01)

(58) Field of Classification Search
CPC ............ B65B 69/00; B67B 7/02; B67B 7/18; B67B 7/182; B67B 2007/188; A47B 81/007; A47B 73/00; A47B 7/28; A47B 7/283; A47B 7/286; B01L 9/06
USPC .............. 53/492, 381.4, 285, 302; 211/85.13, 211/85.18, 74; 422/62, 63, 64, 65, 66
See application file for complete search history.

(56) References Cited

U.S. PATENT DOCUMENTS

| | | | | |
|---|---|---|---|---|
| 3,722,790 | A  * | 3/1973 | Natelson | 494/11 |
| 4,982,553 | A  * | 1/1991 | Itoh | 53/246 |
| 6,257,091 | B1 * | 7/2001 | Cohen et al. | 81/3.2 |
| 7,435,387 | B2 * | 10/2008 | Itoh | 422/547 |
| 8,142,740 | B2 * | 3/2012 | Self et al. | 422/561 |
| 8,562,909 | B2 * | 10/2013 | Schacher | 422/63 |
| 8,703,492 | B2 * | 4/2014 | Self et al. | 436/47 |
| 2005/0214924 | A1 * | 9/2005 | Glaser et al. | 435/252.1 |
| 2007/0110617 | A1 * | 5/2007 | Nagai et al. | 422/65 |

* cited by examiner

*Primary Examiner* — Thanh Truong
*Assistant Examiner* — Dianne Mitchell

(57) ABSTRACT

Apparatus and methods are disclosed for handling a plurality of tubes or vials, and for applying and removing caps to and from tubes or vials, which may be disposed in a rack. The apparatus and methods are well adapted for automated capping and de-capping using generic or off-the-shelf tubes, vials, and caps, such as are commonly used for laboratory samples and reagents.

12 Claims, 17 Drawing Sheets

APPARATUS AND METHODS FOR HANDLING TUBES OR VIALS

CROSS REFERENCE TO RELATED APPLICATION

This application claims priority from U.S. Provisional Patent Application No. 61/597,765, for "Apparatus and Methods for Handling Tubes or Vials," filed Feb. 11, 2012, by Joseph Cohen, et al., the contents of which are incorporated herein by reference as though set forth in full.

STATEMENT REGARDING FEDERALLY SPONSORED RESEARCH

None

TECHNICAL FIELD

The present disclosure relates to the field of laboratory automation and to the capping and de-capping of material containers such as tubes or vials having removable closures. In particular, it applies to any technical field requiring an automated solution to capping and de-capping of tubes or vials, singly, in racks, or otherwise. The apparatus and method are well suited for the capping and de-capping of tubes or vials that are arrayed in a rack.

BACKGROUND

Modern laboratory procedures benefit greatly from automated and/or robotic handling of materials such as samples and reagents. Although specialized multi-compartment containers, such as well plates of various kinds, are of great utility for automating process for which they are suited, often there is a need to handle materials that are stored in individual containers such as vials or tubes. These are manufactured in a variety of geometries and sizes, and typically provided with caps that must be removed for access to the contents and replaced thereafter. Effective automation of the handling, de-capping, and re-capping of containers of this kind has heretofore proved an elusive goal.

Existing systems for capping and de-capping containers having caps that are removed or applied by rotation, such as screw caps, depend upon the use of specially designed caps having features such as slots, sockets, or lugs that can be engaged by a key such as a blade, driver, or wrench of complementary shape. Existing systems also require specially engineered tubes or vials, designed to be disposed in specially engineered racks provided with a locking mechanism to prevent the tubes from spinning in place while the caps are rotated, resulting in increased expense, inviting mechanical failure. The performance of these existing systems is not optimal, due in part to wear and tear on fragile plastic caps from the use of blade-like drivers to physically bind the inside of the caps and apply the force necessary to spin the cap on and off the physically restrained tube or vial. This binding eventually wears out the caps and leads to capping and de-capping failures. Other disadvantages include the added expense of otherwise unnecessary special tubes, caps, and racks, and the additional processing steps, and attendant risk of error, required to transfer substances from their original containers into the specialized tubes and caps. Finally, forcibly spinning multiple caps simultaneously without over-tightening presents a very complex mechanical challenge. A patented clutch mechanism has attempted to address this over-tightening problem, but has proven to be unreliable for automated operations.

A need exists for apparatus and methods that can reliably perform automated capping and de-capping on generic tubes and vials using generic, keyless caps, which may be disposed in a simple, inexpensive rack suitable for storage and automated handling.

SUMMARY

Disclosed herein are methods, devices, compositions, apparatus, and articles of manufacture adapted for capping and de-capping tubes or vials, which may be of standard manufacture, using generic keyless screw caps and using a simple rack that can be easily and inexpensively manufactured. Embodiments of apparatus and methods are provided for rotating vials in situ within a rack by engaging spinning rotors with the vials and imparting a rotation to the vials by friction, while restraining the caps against rotation, also by friction and without the use of a wrench or key. Other embodiments, apparatus, and methods are also disclosed.

Advantages of the present disclosure include, without limitation, the ability to cap and de-cap standard vials not specially adapted to be capped or de-capped. This eliminates the need for users to transfer collections of samples from existing off the shelf tubes or vials into specially designed tubes or vials that are compatible with existing capping and de-capping equipment. The natural clutching mechanism that is created from the interface between the spinning wedges and the bottom and sides of the tubes or vials, as provided in some embodiments disclosed herein, also presents an advantage over the current mechanical clutching systems that have proven to be unreliable.

An object of the disclosure is to provide methods and apparatus for keyless capping and de-capping tubes or vials, that is, without the necessity of applying a turning force via a key such as a blade, driver, or wrench engaged with a slot, socket, lug, or similar force-transmitting feature.

An object of the disclosure is to provide methods and apparatus for capping and de-capping generic tubes or vials including smooth glass and/or plastic tubes and tubes lacking any molded features for gripping.

An object of the disclosure is to provide methods and apparatus for capping and de-capping standard tubes or vials not specially adapted to be capped or de-capped.

An object of the disclosure is to provide methods and apparatus that eliminate the need for users to transfer collections of samples from existing off the shelf tubes or vials into specially designed tubes or vials that are compatible with existing capping and de-capping equipment.

An object of the disclosure is to provide methods and apparatus for capping and de-capping tubes or vials fitted with generic screw caps or other caps whose removal or application involves rotation of the cap relative to the tube or vial.

An object of the disclosure is to provide methods and apparatus for capping and de-capping tubes or vials using only friction for transmitting rotational force to the tubes, vials, and caps.

An object of the disclosure is to provide methods and apparatus for simultaneously capping or de-capping multiple tubes or vials while disposed in a rack.

An object of the disclosure is to provide methods and apparatus for capping and de-capping tubes or vials by rotating the tubes or vials while restraining the caps against rotation.

An object of the disclosure is to provide methods and apparatus for rotating multiple vials within a rack while maintaining stable alignment of the vials by spinning each vial between a plurality of spinning rotors.

An object of the disclosure is to provide methods and apparatus for rotating multiple vials while disposed within a rack, by providing a rack having openings adapted for access by spinning rotors to the vials.

It will be apparent to persons of skill in the art that various of the foregoing aspects, and various other aspects disclosed herein, can be combined in a single device, method, composition, or article of manufacture, thus obtaining the benefit of more than one aspect. The disclosure hereof extends to all such combinations. In addition to the illustrative aspects, embodiments, and features described above, further aspects, embodiments, and features will become apparent by reference to the drawings and detailed description. The foregoing summary is intended to provide a brief introduction to the subject matter of this disclosure and does not in any way limit or circumscribe the scope of the invention(s) disclosed herein, which scope is defined by the claims currently appended or as they may be amended, and as interpreted in the light of the entire disclosure.

Figures are not to scale unless expressly so labeled, and relative positions of objects and components are illustrative. Persons of skill in the art will recognize that many other arrangements, configurations, dimensions, and selections of components are possible and consistent with the disclosure hereof, and are in no way limited to the embodiments shown in the figures.

DETAILED DESCRIPTION

Figure 1A:
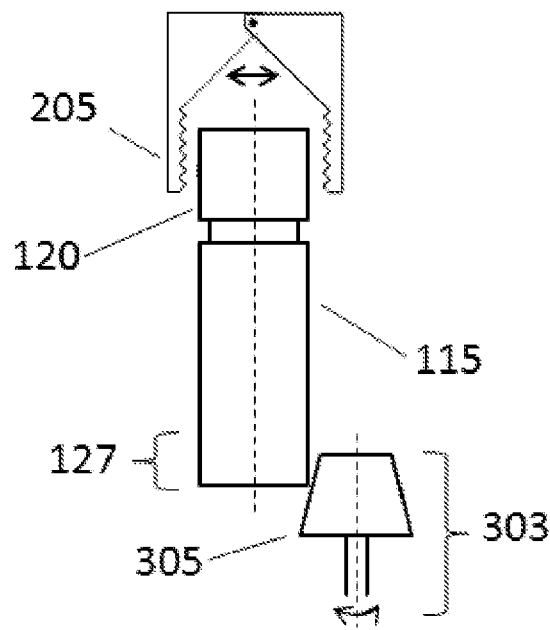
FIGS. 1A, 1B, and 1C depict several embodiments of an apparatus for rotating a vial in relation to a cap.
Figure 1B:
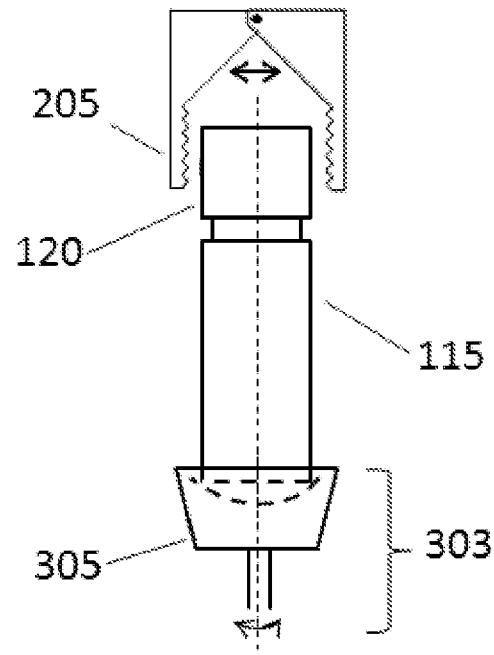
Figure 1C:
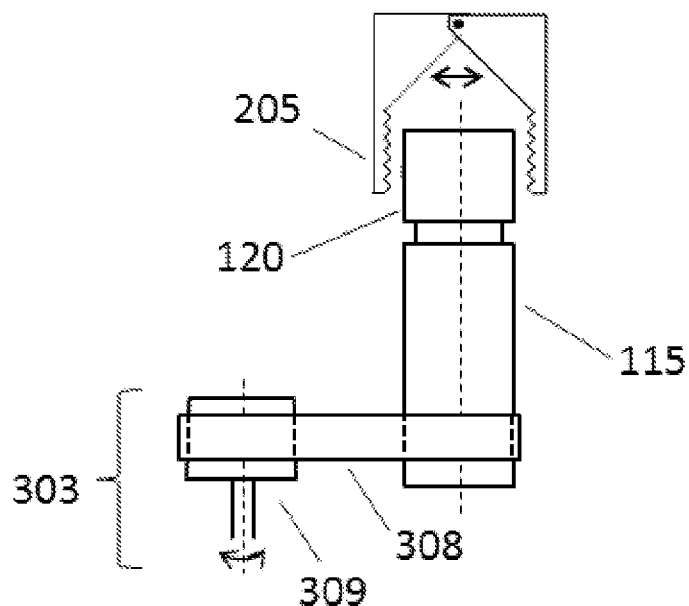

In various embodiments as illustrated schematically in broad overview in FIGS. 1A-1C there is provided an apparatus for rotating one or more vials 115, the apparatus including one or more rotation actuators 303. In some embodiments a vial is adapted to receive a cap 120. In some embodiments a cap gripper 205 is provided to restrain a cap against rotation so that rotation of the vial causes the vial to rotate relative to the cap.

Figure 2:
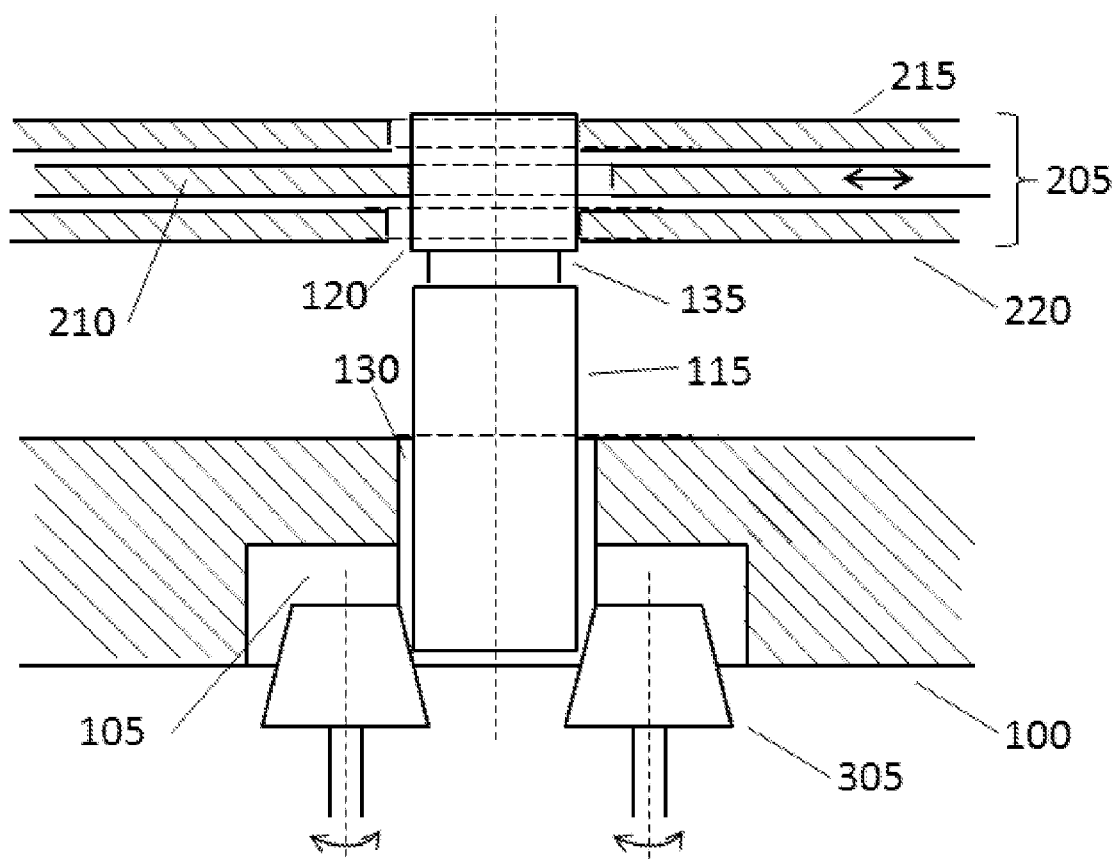
FIG. 2 illustrates schematically an embodiment of an apparatus for capping or de-capping a vial disposed in a rack.
Figure 3:
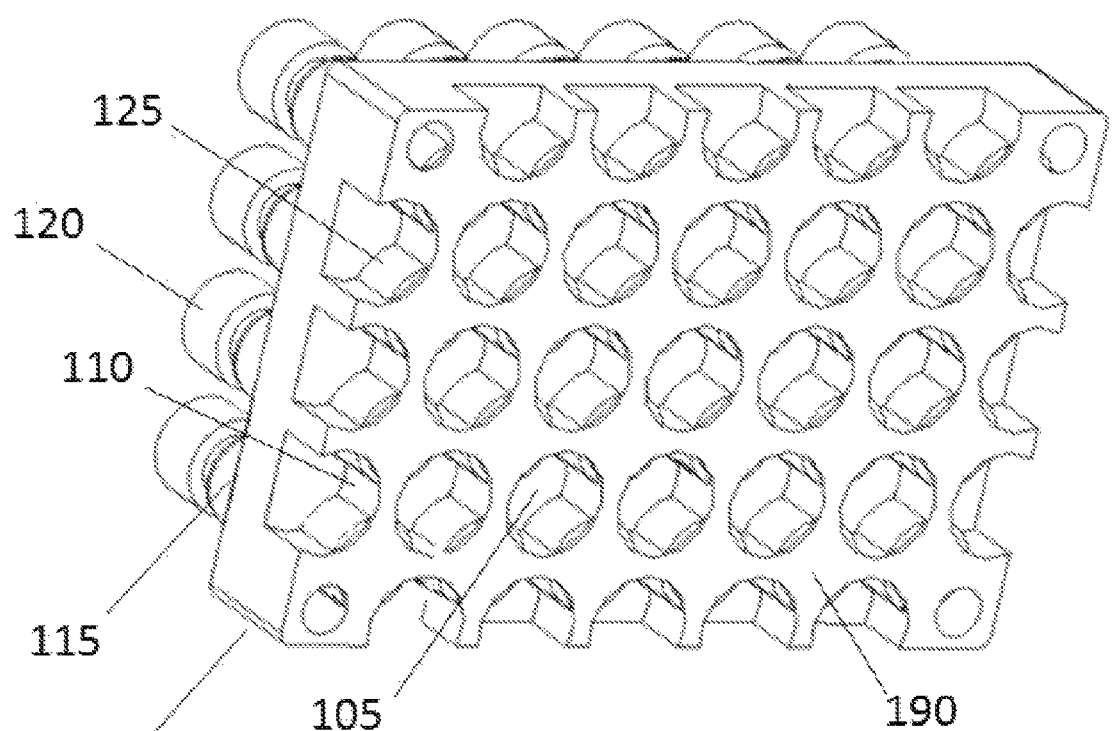
FIG. 3 illustrates an embodiment of a vial rack.

In various embodiments, vials may include containers of any kind operable to contain a material or substance of interest, such as, for example, sample vials, tubes, jars, or test tubes, which may be composed in whole or part of glass, plastic, steel, or any other material capable of being formed into a container and reasonably compatible with any materials desired to be contained therein, and may be of any size, shape, dimension, or geometry operable to contain the materials desired to be contained therein and capable of being disposed in a manner operable to permit a desired range of rotation of the vial by a spinner as disclosed herein. In some embodiments, vials may be generic or off-the-shelf vials or tubes such as, for example, those in which laboratory reagents or samples are packaged in. In some embodiments a vial may be of generally circular cross-section and/or generally cylindrical in shape. In some embodiments as illustrated in FIG. 1A, a vial may have a base portion 127 that is substantially circular in cross-section, such as, for example, a base portion that is generally cylindrical, or cylindrical with a rounded or tapered base. In some embodiments as illustrated in FIGS. 2 and 3, a vial 115 may be disposed in a vial rack 100. In some embodiments a vial may be disposed in a compartment 130 of a vial rack, which may be adapted and configured to allow the vial to rotate about a cylindrical axis or other axis of symmetry within the compartment.

A rotation actuator may be or include any device or component or combination thereof operable to impart a rotation to a vial. In some embodiments a rotation actuator is a keyless actuator, which may include any rotation actuator operable to impart a rotation to a vial wherein the rotation is not imparted substantially by application of a torsional force via engagement of a key such as a driver, blade, or wrench with a torsion-transmitting feature such as, for example, a slot, socket, bolt-like head or other feature having a shape adapted and configured for accepting the driver, blade, or wrench. In some embodiments as illustrated in FIGS. 1A and 1B, a rotation actuator includes a spinner 305, which may include any device or component operable to contact a vial and by rotating impart a rotation to the vial by friction between the spinner and the vial, such as, for example, a rotating wedge or wheel. A spinner may be of any material, composition, size, shape, dimensions, arrangement, position, or geometry operable to impart a rotation to a vial by friction. In some embodiments it will be found useful to employ a spinner composed in whole or part of, or having a surface or vial contacting region composed of, a resilient composition, such as, for example rubber, soft plastic, or an elastomer, to provide tolerance in the positioning of the spinners and vials, distribute forces, and increase friction; and/or to employ a friction-increasing spinner composition and/or surface coating. In some embodiments it will be found useful to employ a tapered spinner having a larger diameter at the base and tapering to a smaller diameter at the end, so that any small differences in vial size or position are more easily accommodated. In some embodiments, the interface between the spinners and the sides and bottoms of the vials may act as a clutching mechanism where the compression pressure and spin velocity can be calibrated such that the spinners will slip and avoid exceeding a proper tightening strength of the cap. In some embodiments a clutch may be provided to allow slippage of the spinner or other rotation actuator so as to limit the torque applied. A spring or other biasing component may also be employed to provide a spinner with a range of motion along its rotational axis, so as to provide additional flexibility in the engagement of the spinner with the vial and to allow for variations between vials due to vial height variation or thread variation. A spinner may be positioned in any relation to a vial operable to impart a rotation to the vial, such as, for example, in an offset engagement with the side or edge of the vial as illustrated in FIG. 1A, or in alignment with the axis of rotation of the vial as illustrated in FIG. 1B. FIG. 1C illustrates by way of example another embodiment of a rotation actuator, including a belt 308 driven by a rotating wheel 309. It will be apparent that many other embodiments are possible of keyless rotation actuators equivalently adapted to impart a rotation to a generally cylindrical or circular object such as a generic tube or vial.

In some embodiments wherein a vial is adapted to receive a cap 120, a cap may be any closure adapted for applying to a vial and configured and adapted to be applied to and/or removed from the vial in whole or part by a motion whereby the cap is rotated relative to the vial. In some embodiments, a cap may be provided with screw threads adapted to engage with screw threads of the cap accepting portion 135 of the vial. In some embodiments a cap may be provided with partial threads and/or one or more flanges or depressions disposed to engage with corresponding elements on a tube or vial upon rotation of the cap relative to the tube or vial. The methods and apparatus disclosed herein will be found useful for handling vials having caps that are securable thereon via any securing modality depending in whole or part upon rotation of the cap relative to the vial. In some embodiments, a cap may have an exterior surface that is in whole or part smooth. In some embodiments, a cap may have an exterior surface that is in whole or part textured for improved friction or gripping, such as, for example, a roughened or corrugated surface. In some embodiments, taking into account that one object of the disclosure is to provide apparatus and methods operable with standard commercial containers and caps which may take on a variety of sizes and geometries, a cap may include one or more features for engagement of a key, driver, or wrench such as a cap manufactured for compatibility with another de-capping device.

In some embodiments as illustrated schematically in FIGS. 1A, 1B, 1C, and 2 wherein a vial is adapted to receive a cap 120 capable of being rotated with respect to the vial, such as, for example, a screw cap, there is provided a cap gripper 205 adapted for gripping the cap and restraining it against rotation, so that when the vial is rotated by the spinner, the vial rotates relative to the cap. A cap gripper may be or include any device or component, of any operable material, composition, size, shape, dimensions, arrangement, or geometry, operable to restrain a vial cap against rotation, such as, for example, opposing jaws disposed to clamp against the cap as illustrated in FIGS. 1A-1C, or opposing thrust plates 210, 215, 220 having openings through which the cap extends and which are translated relative one to the other so as to restrain the cap as illustrated in FIG. 2. In some embodiments a cap gripper operates in a keyless manner, thereby enabling its use with generic caps lacking any features for engagement by a wrench, driver, or blade. In some embodiments, such as illustrated in, for example, FIGS. 6A, 10, and 11, one or more components of a cap gripper may be shared with other cap grippers and/or be integral with an assembly adapted and configured to receive and grip a plurality of caps.

In some embodiments, such as the exemplary embodiments illustrated in FIGS. 2 and 3, there is provided a vial rack 100 adapted to receive one or more vials 115 and permit rotation of the vial(s). A vial rack may have one or more spinner access openings 105 adapted to provide access through which one or more spinners 305 may be engaged with the vial(s) and made to rotate. A plurality of vials in any number and any arrangement may be disposed in a vial rack and engaged by a plurality of spinners, simultaneously or in any operable sequence, so that multiple vials may be capped or de-capped. A spinner may engage a plurality of vials, such as, for example, simultaneously by being positioned so as to contact two or more vials at once, or sequentially by being positioned to contact a vial and then repositioned to contact an additional vial. A vial may be engaged by more than one spinner, such as, for example by being contacted by two or more spinners at once as illustrated in FIG. 2, providing the advantage of tending to center the vial between the spinners and thereby maintain a desired alignment of the vial and avoid binding against the rack. A vial rack may be of any material, size, shape, dimensions, arrangement, or geometry operable to accommodate one or more vials therein in a manner operable to permit a range of rotation of the vial(s) operable for capping or de-capping or another application of interest, and providing access by a spinner or otherwise permitting engagement of a spinner or other rotation actuator with a vial. A vial rack may be adapted and configured to contain, position, and/or segregate vials in any manner operable to dispose the vial(s) in a manner permitting rotation of the vials in accordance with the disclosure hereof, such as, for example, by providing compartments 130 wherein the vials are fully or partially separated by compartment separators 110, and/or by providing bearings, supports, or other components to position the vials. In some embodiments a vial rack may be constructed as a single article such as, for example, a single molded, machined, or 3-D printed piece. In some embodiments a vial rack may be constructed in whole or in part from wire frame or sheet metal or sheet plastic components. In some embodiments a vial rack may include a base or support 190 upon which are disposed other components such as, for example, compartment separators 110. A compartment separator may be disposed on the base by being integral therewith; or by being affixed thereto by any mode of fastening operable to position the separator in a desired position or range of positions relative to the rack, such as, for example, by a fastener, by welding, by an adhesive, or by friction or force fit; or by being affixed to another component or combination of components that is disposed on or affixed to the base. In various embodiments compartment separators may include any one or more components adapted for providing separation between adjacent vials in a rack, such as, for example, walls extending between vial positions from the base; wire frames, rings, and/or posts disposed surrounding and/or between vial positions; or one or more planar components provided with openings corresponding to vial positions and disposed parallel to the base. In some embodiments, separators may, individually or in combination, fully surround all or part of a vial body 125. In some embodiments separators may be disposed to surround a vial body only partially, or provide support only as minimally necessary to prevent unwanted lateral movement of the vial and/or maintain the vial in its compartment. In some embodiments compartment separators may be partially cut away or provided with openings so as to prevent the separators from extending into or interfering with spinner access openings. In some embodiments there may be disposed or employed in a vial rack or any component thereof, anti-friction materials or coatings and/or bearings and/or other components to assist in maintaining desired tube or vial alignment and/or facilitate rotation; locking or restraining mechanisms including, for example, hydraulically or pneumatically actuated bladders or brakes or mechanical restraints or brakes; clutches; springs or biasing components for positioning vials in a desired manner; and/or spinners and/or other mechanisms, which may optionally be integrated with the rack, for engaging, positioning, and/or rotating vials. In vial racks there may optionally be disposed sensors; bar codes, rfid tags or other identification modalities; or any other components or devices deemed useful for the processing and/or handling of the tubes or vials and/or their contents.

Figure 4A:
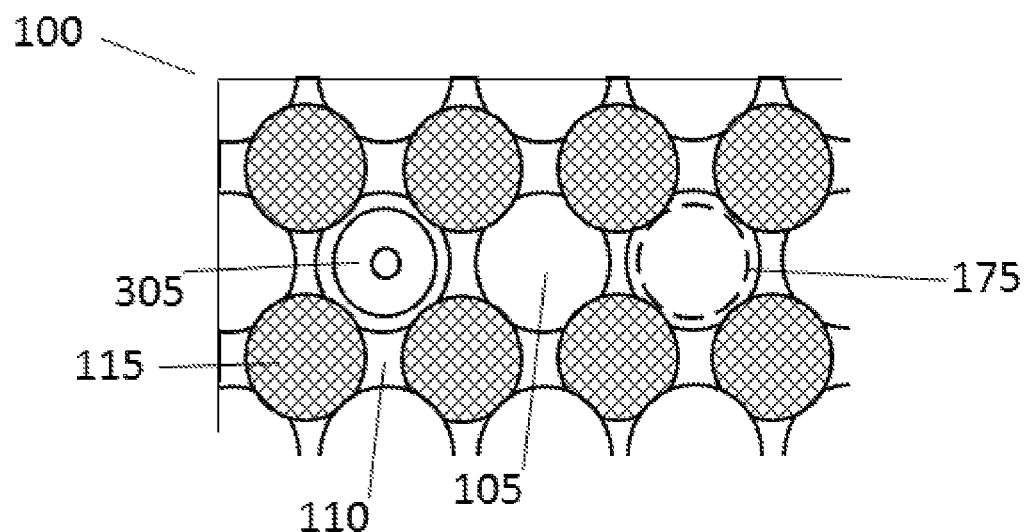
FIGS. 4A and 4B depict arrangements of the vials in two embodiments of a vial rack consistent with the disclosure hereof.
Figure 4B:
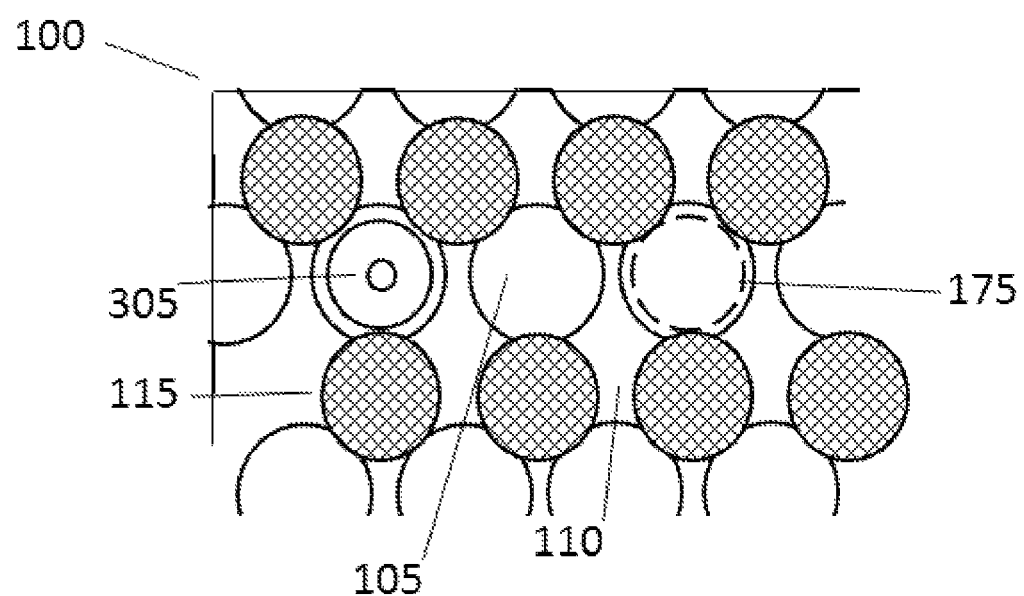

In some embodiments, as illustrated schematically in FIGS. 4A and 4B, a vial rack 100 is adapted and configured, for example via compartment dividers 110 defining compartments, to position a plurality of vials 115 in an arrangement wherein the axes of rotation of the vials with respect to the caps are approximately parallel one to another (perpendicular to the plane of the figure), and the base portions or spinner-contact portions of the vials lie approximately in a plane approximately perpendicular to the axes of rotation, with spinner access openings 105 positioned in approximate alignment with the interstices 175 between the vials so that a rotating spinner 305 having a generally circular cross section aligned within a spinner access opening is in contact with two or more vials adjacent to the spinner access opening. It will be apparent that many such arrangements and/or rack configurations are possible, wherein, for example, each vial is contacted by four spinners as shown in FIG. 4A, or by three spinners as shown in FIG. 4B. It will be found useful in some embodiments to employ arrangements whereby vials are contacted by an approximately symmetric arrangement of spinners, so as to ensure balanced forces tending to center the vials between the spinners, and/or wherein spinners are of approximately uniform circumference so that the rates of motion of the surfaces of the spinners at the points of contact with the vials are maintained relatively equivalent so as to distribute the applied force evenly around the circumference of each vial. Nevertheless, the methods and apparatus hereof can also be applied to non-symmetric and non-uniform arrangements of spinners and vials, provided that these are arranged and sized such that effective engagement of at least one spinner with each vial can be achieved.

Figure 5:
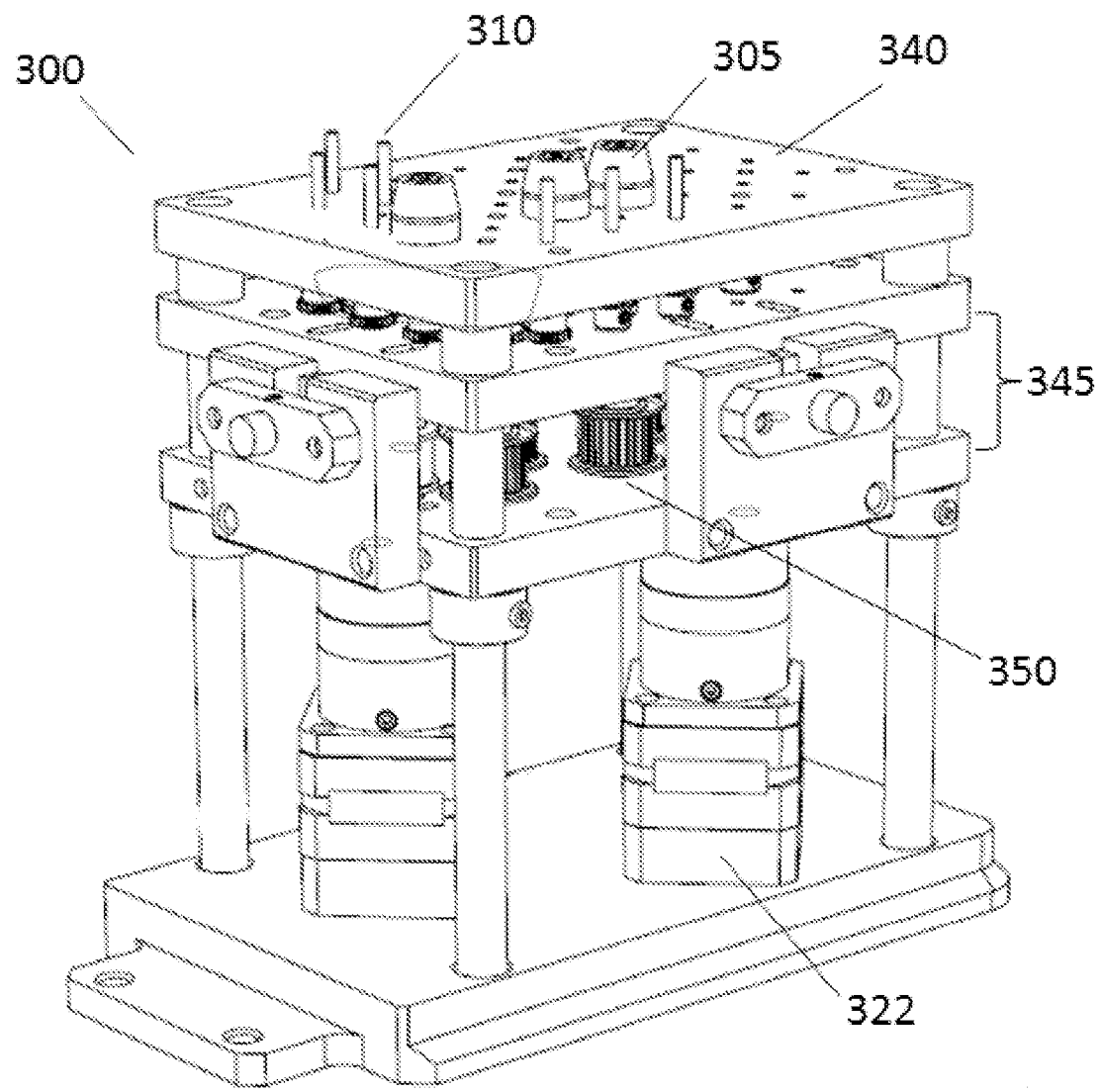
FIG. 5 shows an embodiment of a spinner assembly.

In some embodiments a spinner assembly is provided wherein are disposed a plurality of spinners. In various embodiments spinners may be arranged, sized, adapted, and configured in a spinner assembly in an arrangement alignable for rotation-imparting engagement of a plurality of vials, which may include any arrangement operable to align with and engage at least one spinner with each of a plurality of vials in a rack or other disposition with which the spinner assembly is intended to be used, the spinners being aligned and positioned in an arrangement whereby each spinner is operable to contact and impart a rotation to a vial with which it is engaged by rotating while in contact with the vial and imparting a rotation to the vial by friction between the spinner and the vial. FIG. 5 depicts an exemplary embodiment of a spinner stage including a spinner assembly 300, including a base 340 in which a plurality of spinner shafts 310 are disposed in bearings. Spinners 305 are mounted on the spinner shafts, which are rotated by one or more transmissions 345 driven by one or more spinner actuators 320. In various embodiments, a spinner actuator may include any device, component, or combination thereof operable to provide motive power for rotating a spinner shaft, such as, for example, an electric motor, a hydraulic or air motor, or a solenoid, and may include one or more sensors and/or controllers. In some embodiments, a transmission may include any one or more devices or components or combination thereof operable for transmitting motive power from an actuator to one or more spinner shafts, such as, for example, one or more gear trains, belt and pulley arrangements, chain and sprocket arrangements, rack and pinion arrangements, hydraulic clutches or transmissions, and/or other components for converting a motion of an actuator into a rotation of a spinner shaft. A transmission may include one or more devices, components, or combinations thereof for controlling and/or limiting the motive power or force supplied to a spinner and/or allowing slippage of a spinner under load, such as a clutch or hydraulic drive. In an exemplary embodiment such as illustrated in FIG. 5, spinner shafts may be driven by a gear train 350 powered by an electric motor 322. In some embodiments a spinner assembly may include any other devices and components useful for adapting the spinner assembly to an application of interest. In some embodiments a spinner assembly may include structural or other components for supporting and/or positioning the various components and/or integrating the various components into a unit or stage. In some embodiments a spinner assembly may include one or more sensors, actuators, controllers, or other components for determining and controlling the action of any component or combination of components.

In some embodiments a cap gripper assembly is provided wherein are disposed a plurality of cap grippers. In various embodiments cap grippers may be arranged, sized, adapted, and configured in a cap gripper assembly in any manner compatible with the characteristics, dimensions, and geometry of a rack and/or vials with which the cap gripper assembly is intended to be used. In some embodiments, keyless cap grippers are employed, providing advantages such as avoiding damage to caps, enabling the use of generic caps lacking any features to which a key or wrench-type drive might be applied, and obviating the need for aligning a key or wrench-type drive with a corresponding cap feature.

Figure 6A:
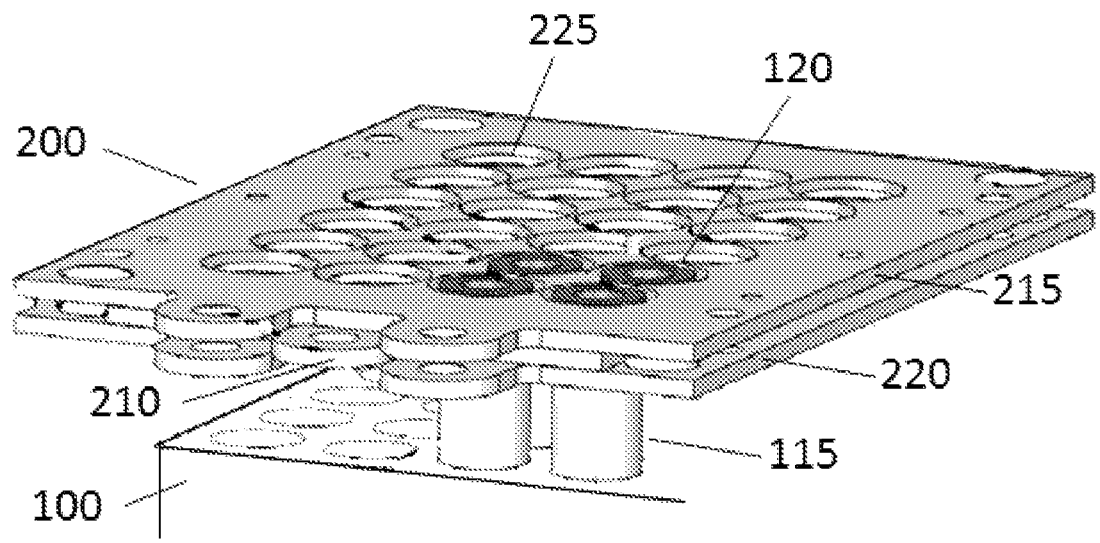
FIG. 6A depicts an embodiment of a cap gripper assembly.
Figure 6B:
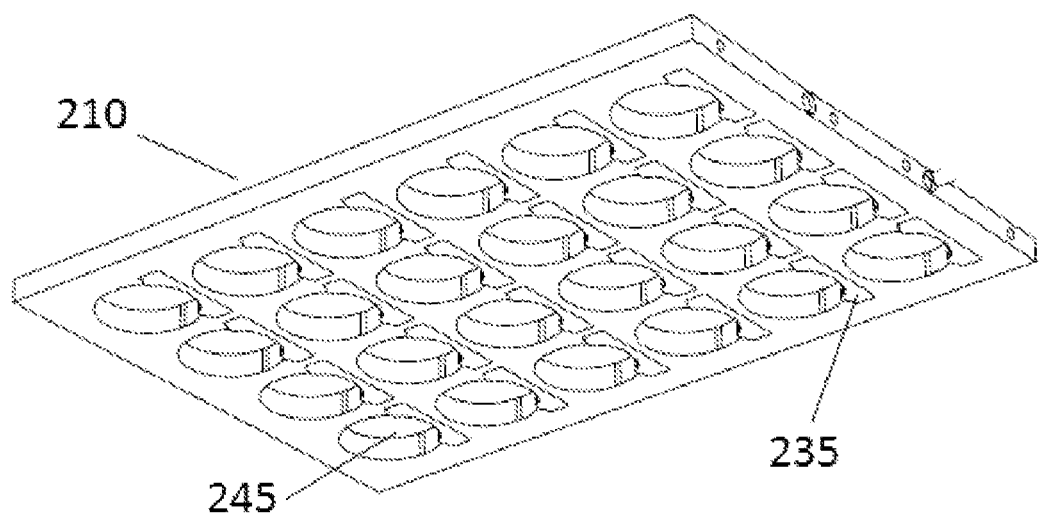
FIG. 6B depicts an embodiment of a cap gripper thrust plate.

In an exemplary embodiment as illustrated in FIG. 6A, a cap gripper assembly includes a thrust plate 210 sandwiched between two counterthrust plates 215, 220. The thrust plate and counterthrust plates are provided with openings 245 defining, in whole or part, cap receiving spaces 225 that align with the caps 120 and/or cap accepting portions of vials 115 disposed in a rack 100. When the thrust plate is translated relative to the counterthrust plates, the cap receiving space occupied by the caps is constricted and the caps are compressed against the walls of the openings in the thrust and counterthrust plates, thereby opposing any rotation of the caps by a friction force between the caps and the walls of the thrust and counterthrust plates.

Figure 7:
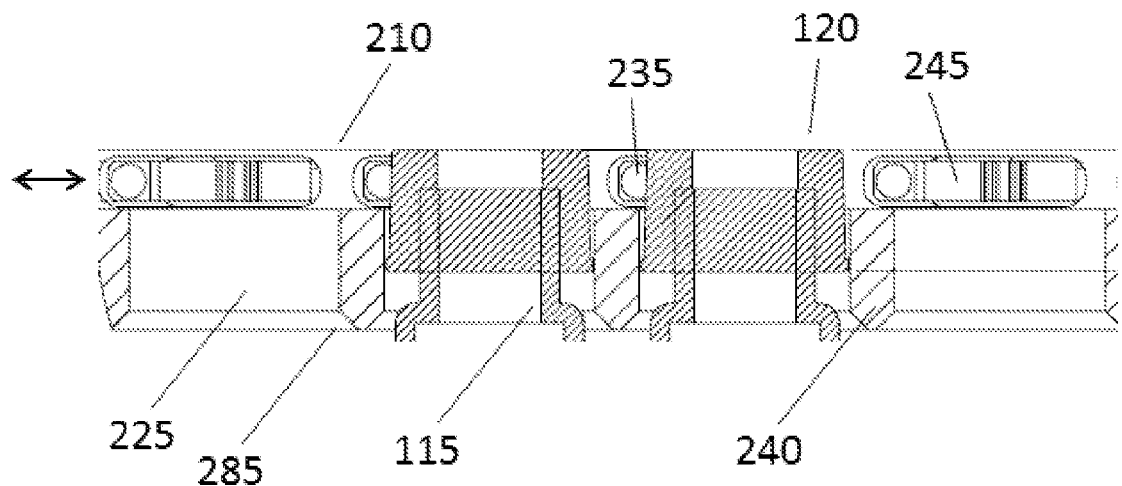
FIG. 7 shows a partial view of an embodiment of a cap gripper assembly.
Figure 9A:
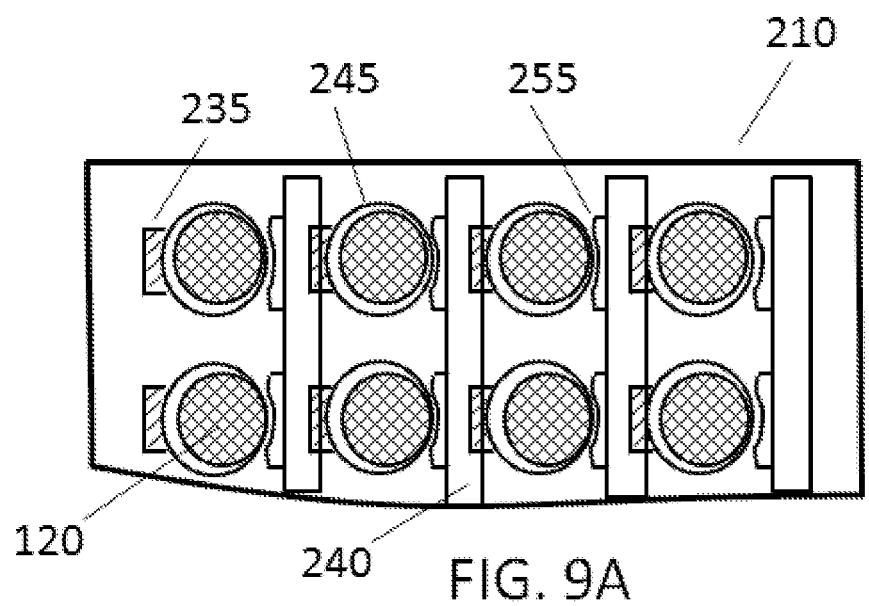
FIG. 9A shows a partial view of an embodiment of a cap gripper assembly in a release configuration.
Figure 9B:
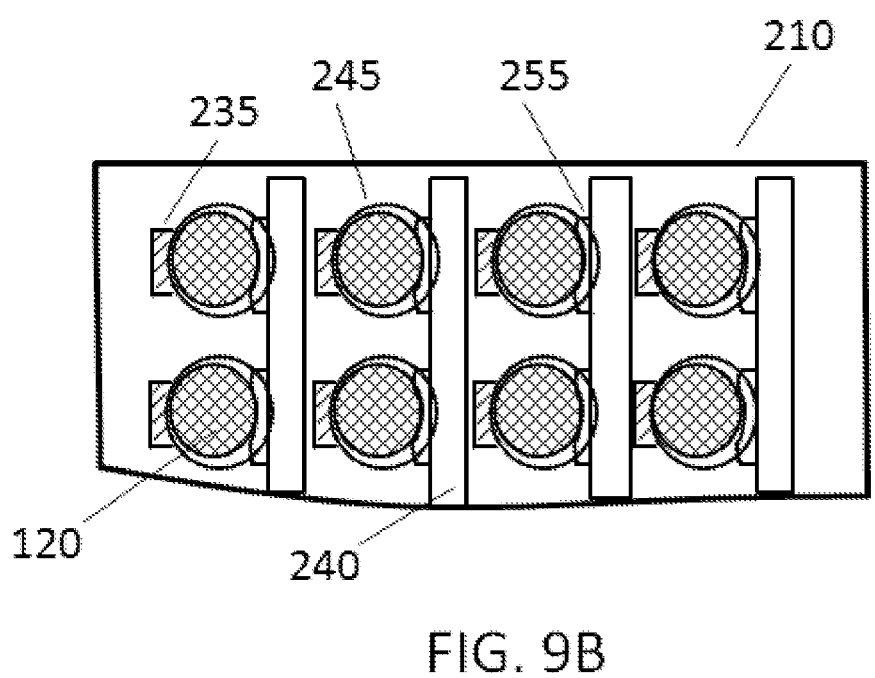
FIG. 9B shows a partial view of an embodiment of a cap gripper assembly in a gripping configuration.

In another exemplary embodiment as illustrated in FIG. 7, a cap gripper assembly may include a thrust plate 210, and one or more impingement bars 240 (here oriented perpendicular to the plane of the figure). The thrust plate is provided with openings 245 which together with the space between impingement bars define in whole or part a cap receiving space 225 adapted to receive a cap 120 which may be fitted to a vial 115. When the gripper assembly is in a cap release configuration as illustrated in FIG. 9A, the thrust plate is positioned so that the cap receiving opening 245 is sufficiently unobstructed by an impingement bar 240 so as to admit a cap in the opening. When the gripper assembly is transitioned to a cap gripping configuration, such as, for example, by translating the thrust plate 210 relative to the impingement bar(s) 240 as illustrated in FIG. 9B, the cap 120 is then gripped between the wall or edge of the thrust plate opening and the impingement bar. In some embodiments, a cap gripper assembly includes a thrust plate provided with a plurality of openings and defining a boundary region surrounding each opening, each boundary region enclosing all or part of a cap receiving space and including an impingement contact, and a gripper actuator disposed and configured to displace the thrust plate generally in the plane of the thrust plate to displace the impingement contacts into the cap receiving spaces.

Figure 8:
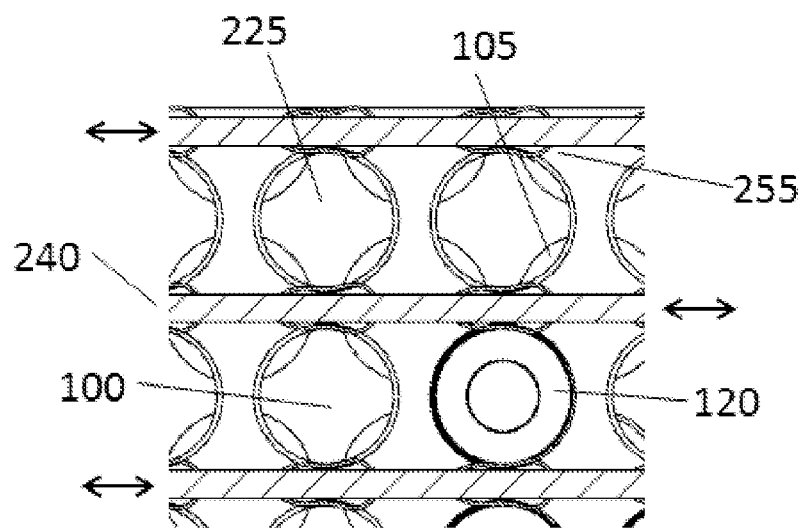
FIG. 8 shows a partial view of another embodiment of a cap gripper assembly.
Figure 10:
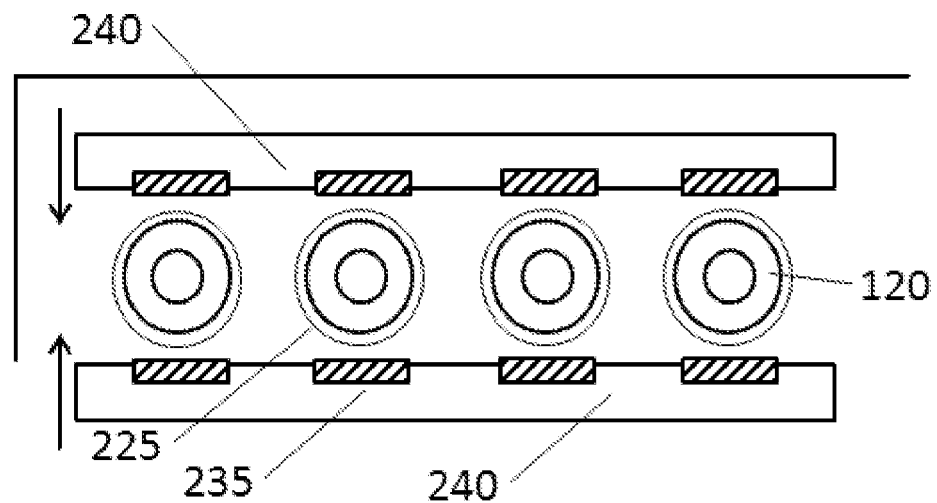
FIG. 10 shows a partial view of an alternative embodiment of a cap gripper assembly.
Figure 11:
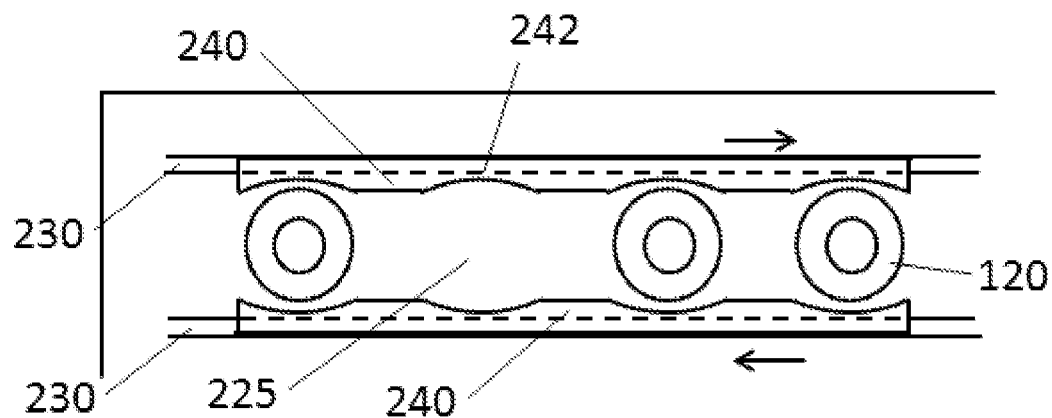
FIG. 11 shows a partial view of another alternative embodiment of a cap gripper assembly.

In some embodiments as illustrated in FIG. 8, a cap gripper assembly may include impingement bars 240 disposed in parallel fashion enclosing all or part of a cap receiving space 225 between the impingement bars. The impingement bars may be provided with springs 255 or other impingement contacts for engaging a cap 120 disposed in the cap receiving space. The impingement bars may be translated longitudinally or transversely to engage the cap(s) with the springs or to release the caps therefrom. In some embodiments a thrust plate may be employed in addition to the impingement bars, such as, for example, in the manner illustrated in FIG. 7. In some embodiments as illustrated in FIG. 10, a cap gripper assembly may include one or more impingement bars 240, which may be made to grip a plurality of caps by translating the impingement bar(s) laterally against the caps. In some embodiments as illustrated in FIG. 11, impingement bars 240 may be provided with indentations or narrowed regions 242 adjacent to a cap receiving space 225, and may be disposed and configured to translate longitudinally, such as in a track 230, thereby impinging the wider portion of the impingement bar against the caps.

In some embodiments as illustrated in, for example, FIGS. 6B, 9A, 9B, and 10, there is provided an impingement contact 235 which may be positioned at a point of contact between a cap gripper component and a cap, such as, for example, bordering an opening 245 in a thrust plate 210 (FIG. 6B) or counterthrust plate or at the contact point of an impingement bar 240 (FIG. 10). An impingement contact may be composed of a resilient material, such as, for example, rubber, plastic, or an elastomer, so as to better distribute and equalize the force of the thrust plate over the plurality of caps and/or protect the cap from damage and/or improve friction and gripping; a friction-increasing material to increase the friction and restraining force between the cap gripper and the cap; a spring or other biasing component such as, for example, the impingement bar springs 255 as illustrated in FIGS. 8, 9A and 9B; or any other material having properties deemed useful for an application of interest. The impingement contact, particularly at the point of contact with a cap, may be shaped, surface treated, or otherwise optimized for improved engagement with a cap, increased friction, improvement of wear characteristics of the contact or cap, or for any other purpose. An impingement contact may be integral with a cap gripper component, such as, for example, a thrust plate, counterthrust plate, impingement bar, or gripping jaw, or may be or include a separate component.

In some embodiments a cap gripper assembly may include any other devices and components useful for adapting the cap gripper assembly to an application of interest. In some embodiments a cap gripper assembly may include structural or other components for supporting and/or positioning the various components and/or integrating the various components into a unit or stage. In some embodiments a cap gripper assembly may include one or more sensors, actuators, controllers, or other components for determining and controlling the action of any component or combination of components. In some embodiments a cap gripper and/or cap gripper assembly may include a chamfered, flared, or tapered region, to assist in positioning a cap within the gripper in a desired alignment, such as, for example, the chamfered opening 285 to the cap receiving space 225 as illustrated in FIG. 7.

Figure 12:
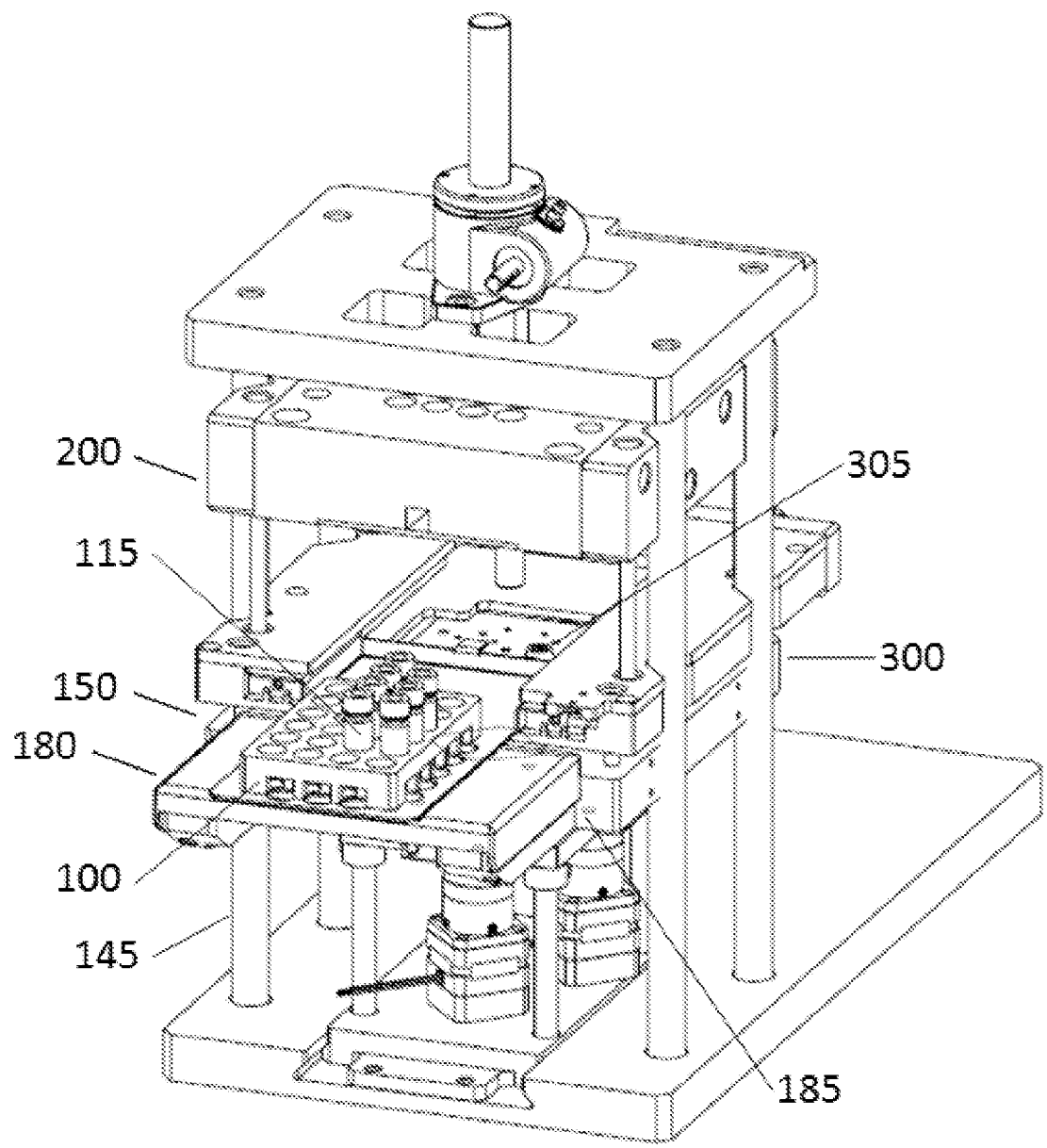
FIG. 12 is a perspective view of an embodiment of an apparatus for capping or de-capping a plurality of vials disposed in a rack.
Figure 14:
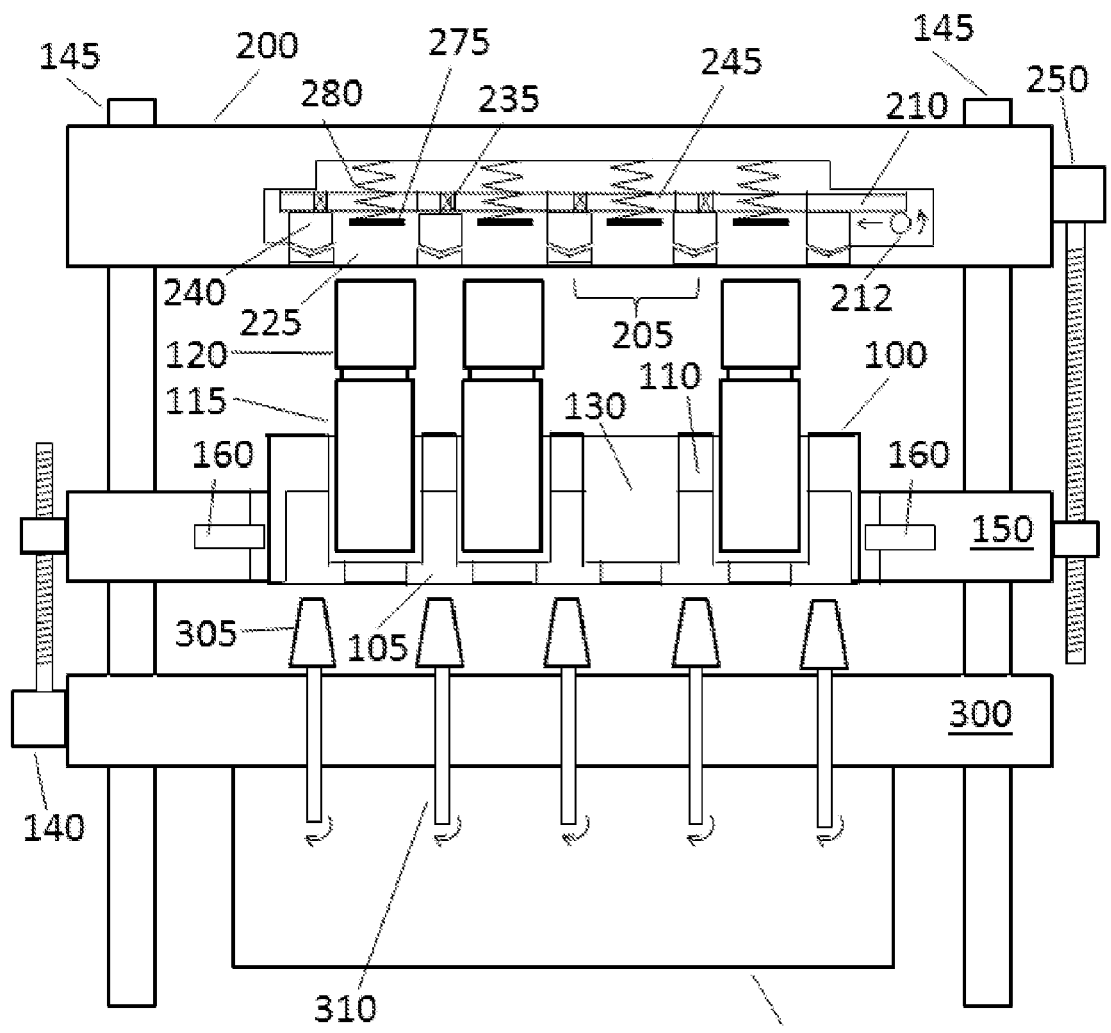
FIG. 14 depicts schematically in cross-section an embodiment of an apparatus for capping or de-capping a plurality of vials disposed in a rack, in a disengaged configuration.

In some embodiments of an apparatus according to the disclosure hereof, there is provided a rack holder. A rack holder may be or include any apparatus, incorporating any one or more devices and/or components, operable for supporting a vial rack, for receiving and/or securing a vial rack, and/or for positioning and/or aligning a vial rack relative to a spinner assembly, a cap gripper assembly, or otherwise. In some embodiments as illustrated in FIG. 12, there is provided a rack holder 150 which may include a rack receiver 180, such as, for example, a drawer, shelf, or tray, which may be affixed to the rack holder, and/or mounted in or on a rack receiver mount 185 which may include, for example, one or more slides, pivots, hinges, actuators, or mechanisms for providing for movement of the rack receiver between a rack loading/unloading position wherein the rack receiver is positioned to allow placement of a vial rack therein, and a retracted position, such as, for example, a position in which a vial rack disposed in the rack receiver is aligned for engagement with a spinner assembly, or cap gripper assembly, and/or any other position found useful for an application of interest. In some embodiments, a rack receiver may be manually transitioned from one position to another. In some embodiments a rack receiver is positioned mechanically and/or under the control of a controller, allowing for integration with automated devices to load and unload the rack tray, cap gripper assembly, and/or caps. As illustrated in FIG. 14, one or more clamps 160 may be provided for restraining a rack 100 against movement.

The various apparatus and components disclosed herein may be employed separately or combined in an apparatus in any manner operable for an application of interest. In an exemplary embodiment as illustrated in FIG. 12, there is provided an apparatus including a rack holder 150 adapted and configured to receive a rack 100 which may contain a plurality of vials 115; a spinner assembly 300 which may include spinners adapted and configured to align with and engage vials through spinner access openings in the rack; and a cap gripper assembly 200, which may be adapted and configured to position caps gripped therein in alignment for engagement with vials. In some embodiments such as the exemplary embodiment illustrated in FIG. 12, it may be found useful to dispose a spinner assembly, rack holder, and cap gripper assembly in stages and/or on one or more support structures, such as, for example, one or more support columns 145 so as to facilitate alignment and positioning of the spinner assembly, rack holder, and/or cap gripper assembly relative one to another. In some embodiments, a spinner assembly, rack holder, and/or cap gripper assembly may include or be incorporated in or mounted upon any support or structure operable for an application of interest. For example, in some embodiments, a spinner assembly, rack holder, and/or cap gripper assembly may include or be incorporated in or mounted upon a robotic arm or other positionable and/or controllable support. In some embodiments, a spinner assembly, cap gripper assembly, vial rack, rack holder, or other components may be adapted and configured to engage in a predetermined manner one with the other to ensure correct alignment, prevent insertion in a wrong direction, and/or for compatibility.

Figure 13:
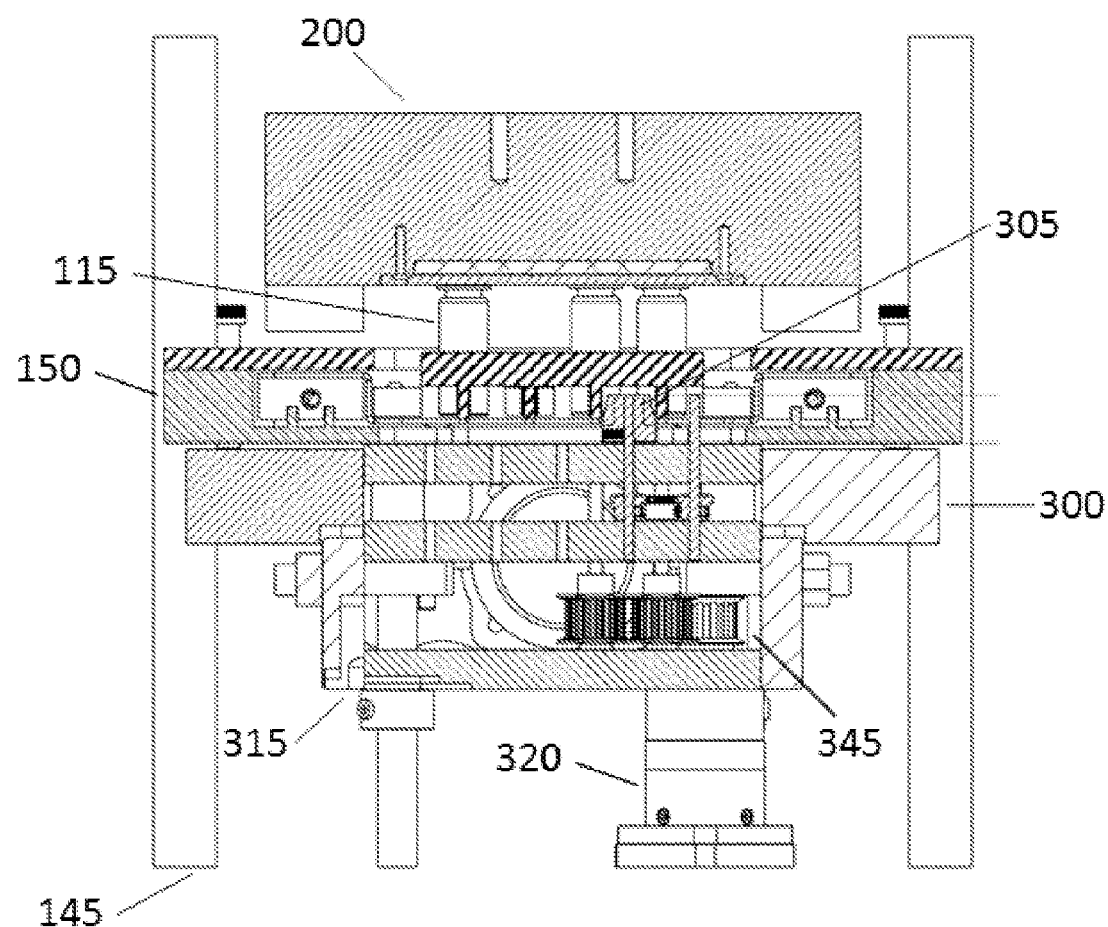
FIG. 13 is a schematic depiction in cross-section of an embodiment of an apparatus for capping or de-capping a plurality of vials disposed in a rack.

In some embodiments such as the exemplary embodiment illustrated in FIG. 13, there is provided a spinner assembly 300, a rack holder 150, and a cap gripper assembly 200, each incorporated in a stage for mounting to one or more supports 145, one or more of which are adapted and configured to move relative to the support so as to engage a spinner 305 of the spinner assembly with a vial 115 disposed in a vial rack positioned in the rack holder and/or to position the cap gripper assembly 200 so as to dispose within a cap receiving space of the cap gripper assembly a cap with which a vial is fitted, and/or so as to disengage the cap gripper assembly relative to the vial rack and/or disengage the vial rack relative to the spinner assembly.

Figure 15:
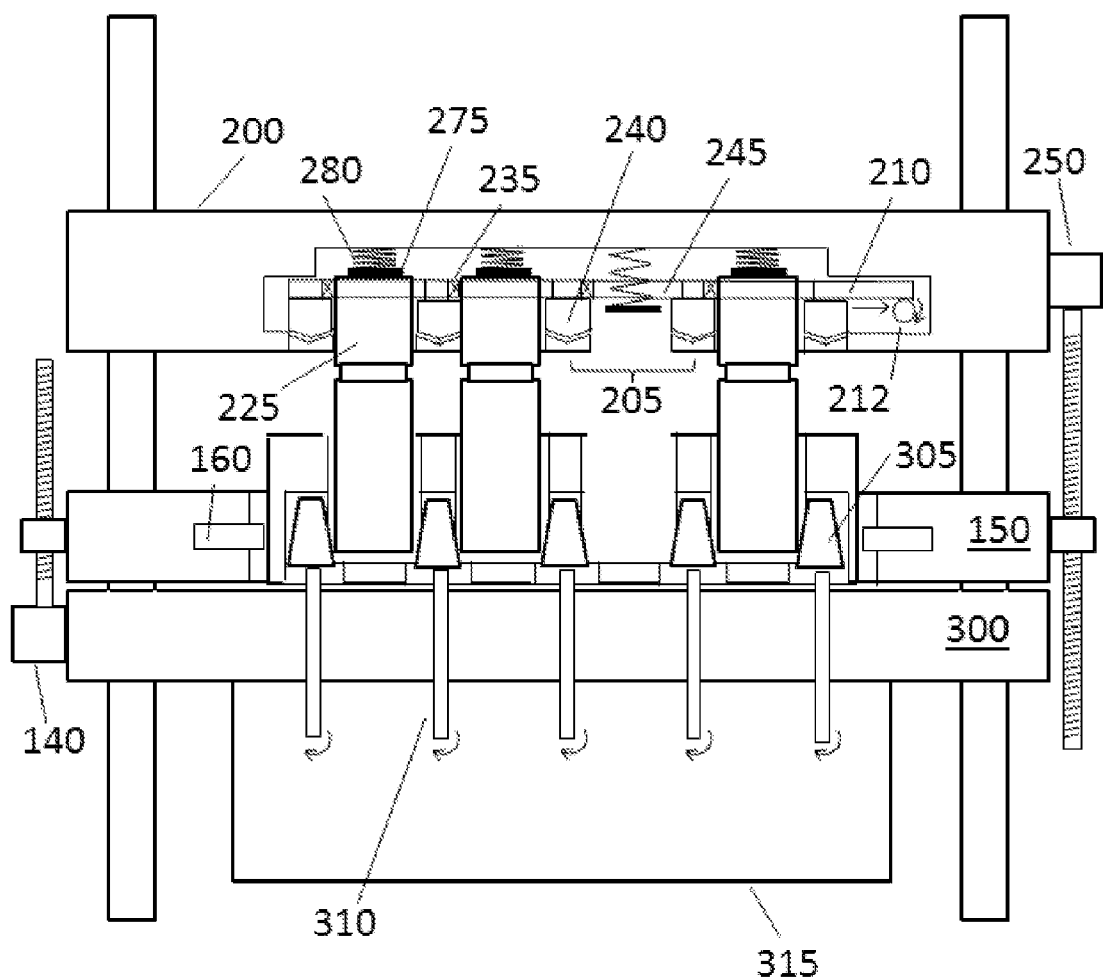
FIG. 15 depicts schematically in cross-section an embodiment of an apparatus for capping or de-capping a plurality of vials disposed in a rack, in an engaged configuration.
Figure 16:
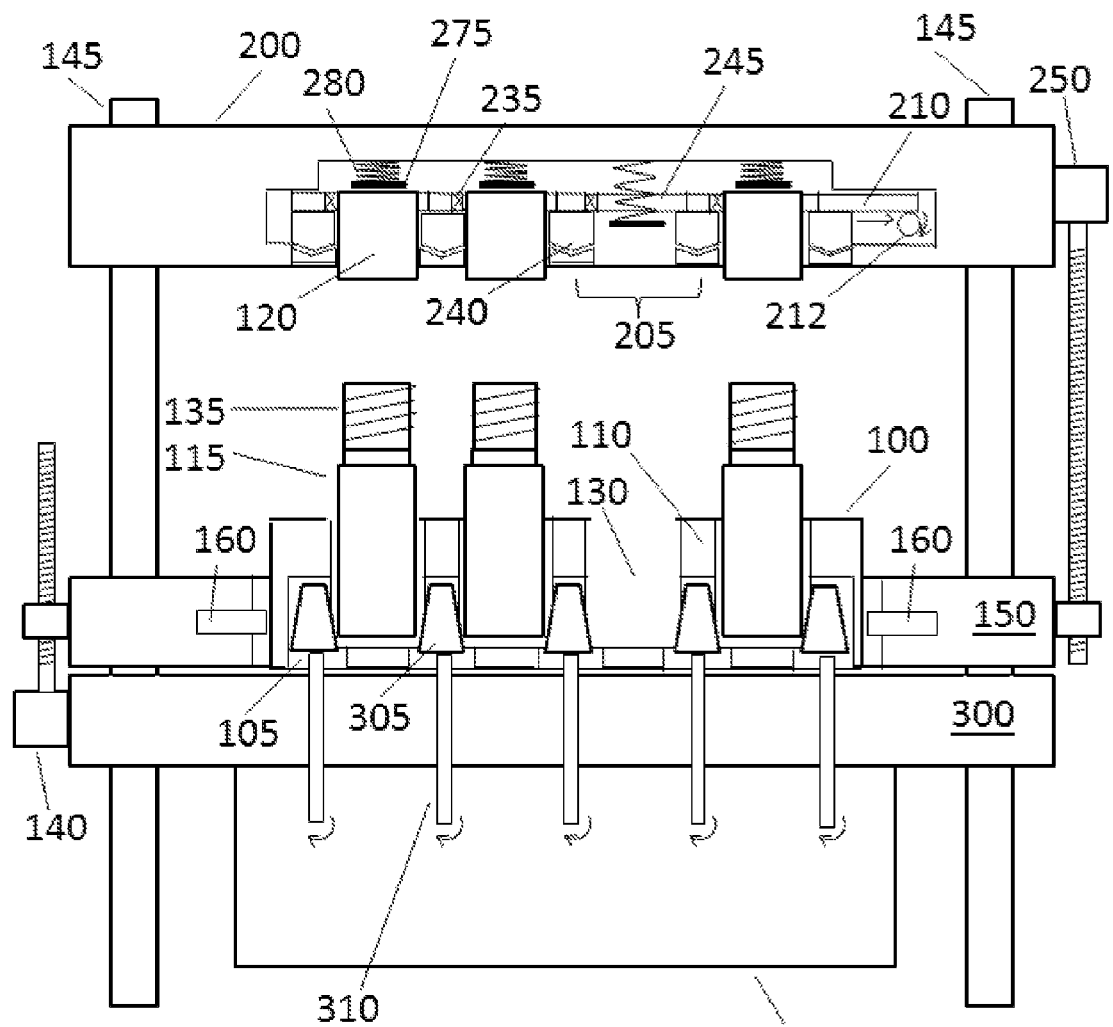
FIG. 16 depicts schematically in cross-section an embodiment of an apparatus for capping or de-capping a plurality of vials disposed in a rack after de-capping has occurred.

In some embodiments such as the exemplary embodiment illustrated schematically in FIGS. 14-16, an apparatus may include any one or more of: a rack holder stage including a rack holder 150 for receiving a vial rack, which may contain a plurality of vials 115; a vial spinner stage or assembly 300 including a plurality of spinners 305, wherein each spinner may be positioned to align with a spinner access opening 105 of a vial rack 100 when a vial rack is present and positioned for engagement with the spinner stage or assembly; a spinner drive 315 for imparting rotation to the spinners, which may include an actuator 320 such as, for example, a motor, and may include a transmission 345; a cap gripper stage or assembly 200 including a plurality of cap grippers 205, each cap gripper enclosing all or part of a cap receiving space 225; one or more gripper actuators 212 for selectably actuating the grippers to a cap gripping configuration or a cap release configuration; a vial rack positioning actuator 140 for selectably positioning a vial rack and/or rack holder and a vial spinner stage in a desired relation one to the other, such as, for example, an engaged position such as that shown schematically in FIGS. 15 and 16 wherein the vial rack 100 and vial holder stage 150 are positioned relative to the vial spinner stage 300 whereby each of the vials 115 is in contact with at least one spinner 305, or a disengaged position, such as that shown in FIG. 14 wherein the vial rack is disengaged from the vial spinner stage, such as to allow loading or unloading of the vial rack from the apparatus; a cap gripper stage positioning actuator 250 for selectably positioning the cap gripper stage 200 relative to a rack holder stage 150, spinner assembly, support, or other component in a desired relation one to the other, such as, for example, an operating configuration such as that shown in FIG. 15 wherein the cap accepting portion of each of the vials is positioned in the cap receiving space 225 of a gripper 205, or a displaced configuration such as that shown in FIG. 16 wherein the cap gripper stage and the rack holder are displaced one from the other relative to the operating configuration.

In some embodiments, there may be provided, as part of a cap gripper assembly or stage or otherwise, a cap biasing component for applying a force to a cap. A cap biasing component may be or include any device or component or combination of components operable to impose a force against a cap positioned in the cap receiving space of a cap gripper or otherwise, such as, for example, a spring, piston, lever, or cam. In some embodiments, as illustrated schematically in FIGS. 14-16, there is provided a cap biasing component including a spring 280 and a puck 275 acted on by the spring, to provide a biasing force on a cap 120. In some embodiments it will be found useful to apply a biasing force to a cap during de-capping or capping so as to assist in maintaining a desired pressure between a vial and the spinners against which it is engaged. In embodiments wherein a plurality of vials are capped or de-capped, the use of a cap biasing component also assists in equalizing the pressure of the vials against the spinners, and allows for some variation in vial and/or cap dimensions.

In some embodiments, an apparatus may include one or more sensors, actuators, or controllers, which may be employed to sense and/or report any property or condition of interest and determine, control, and/or effect any action in response thereto or according to a program or in any other manner useful for an application of interest. By way of example, in some embodiments as illustrated schematically in FIG. 17, an apparatus including one or more of a spinner assembly 300, a rack holder 150 and/or a cap gripper assembly 200 may further include one or more sensors, actuators, and/or controllers, such as, for example, a cap gripper position sensor 260 for sensing the position of the cap gripper assembly relative to a support 145, rack holder, spinner assembly, or other component; a cap gripper assembly status sensor 270 for sensing a condition or property relating to the cap gripper assembly and/or a component thereof, such as, for example, whether a cap gripper is in an engaged position with a cap or an open or release position; a rack holder position sensor 155 for sensing the position of the rack holder relative to a support, spinner assembly, cap gripper assembly, or other component; a rack holder status sensor 165 for sensing a condition or property relating to the rack holder and/or a component thereof, such as, for example, whether a rack receiver is in an extended or retracted position and/or whether a rack is present in the rack holder; a spinner assembly position sensor 325 for sensing the position of the spinner assembly relative to a support, rack holder, cap gripper assembly, or other component; and/or a spinner assembly status sensor 335 for sensing a condition or property relating to the spinner assembly and/or a component thereof, such as, for example, whether a spinner is engaged with a vial, whether a spinner is in motion, or a force or pressure of a spinner against a vial. It will be apparent that sensors may be employed to sense and/or report many other properties and/or conditions of possible interest, and that the foregoing enumeration is intended merely to provide illustrative examples. In various embodiments, a sensor may be or include any device or component operable for sensing, detecting, and/or reporting a condition or property of interest, such as, for example, a position sensor, a strain gauge, a micro switch, a tension or compression sensor, or a current or voltage sensor. In some embodiments an apparatus includes a detection system, which may include one or more sensors, adapted and configured to detect whether a vial has been successfully capped or de-capped and optionally issue an alert or error message as appropriate.

Figure 17:
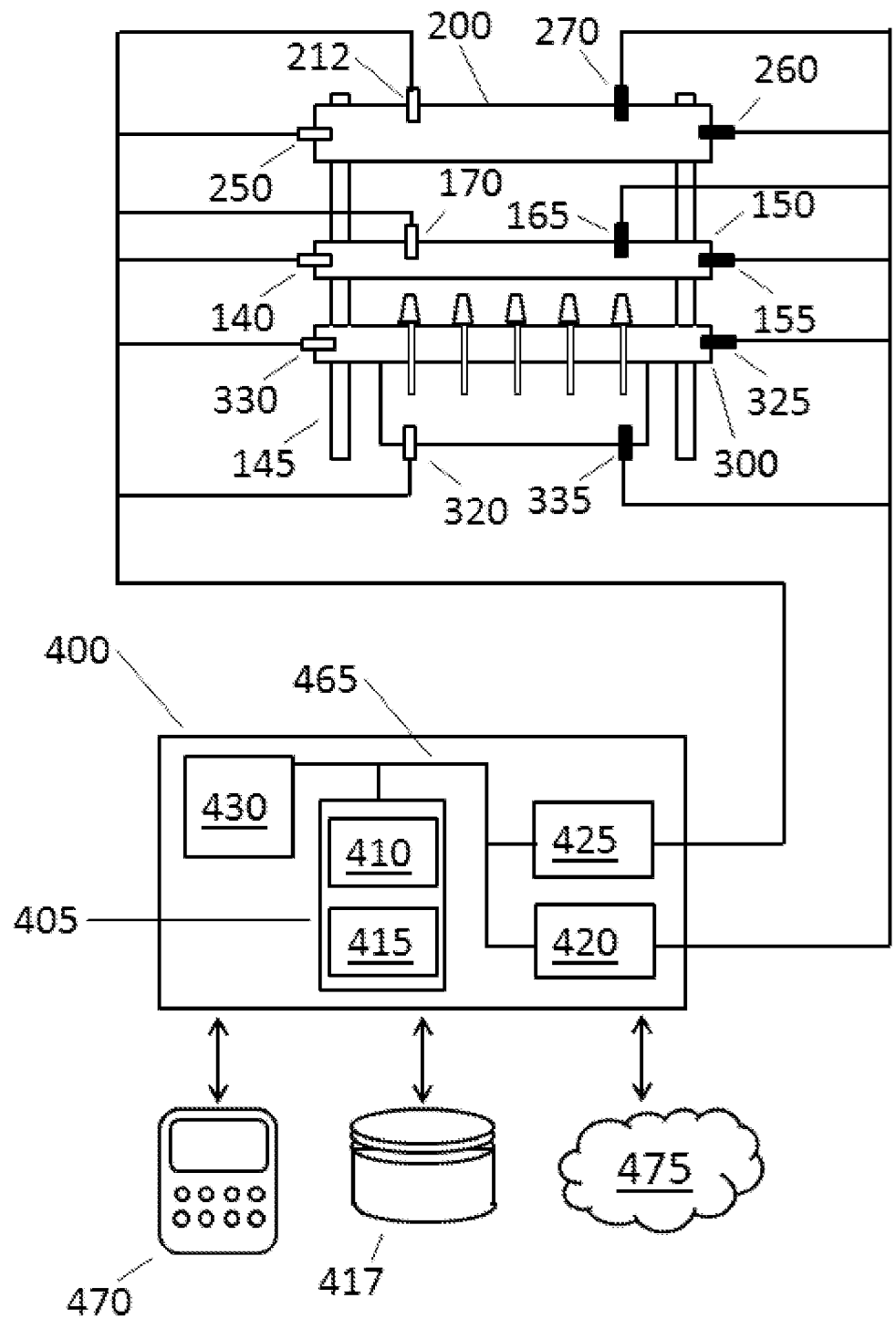
FIG. 17 depicts schematically controller, sensing, and actuating components of an embodiment of an apparatus for capping or de-capping vials.

In some embodiments as illustrated in FIG. 17, an apparatus may further include one or more actuators, such as, for example, a cap gripper positioning actuator 250 for positioning the cap gripper assembly relative to a support, rack holder, spinner assembly, or other component; a cap gripper actuator 212 for actuating a cap gripper to an engaged or release position; a rack holder position actuator for positioning the rack holder relative to a support, spinner assembly, cap gripper assembly, or other component; a rack holder actuator 170 for positioning a rack receiver in a desired position; a spinner assembly position actuator 330 for positioning the spinner assembly relative to a support, rack holder, cap gripper assembly, or other component; and/or a spinner assembly actuator for engaging spinners with vials, for causing spinners to rotate, or for any other purpose. It will be apparent that actuators may be employed in many other possible ways consistent with the disclosure hereof, and that the foregoing enumeration is intended merely to provide illustrative examples. In various embodiments, an actuator may be or include any one or more devices or components operable for effecting a desired motion and/or positioning a component in a desired position, such as, for example, an electric motor, a solenoid, or a hydraulic or pneumatic motor or drive, a motor driven screw, a gear train, a rack and/or pinion, a chain, a sprocket, a pulley, a belt, a hydraulic or pneumatic piston, a clutch, or any other of the many devices or components operable for producing rotary motion, linear motion, and/or motion on a desired path or trajectory.

In some embodiments as illustrated in FIG. 17, an apparatus may include a controller 400, which in various embodiments may include one or more of a processor 430 optionally interfaced via a bus 465 or other communication channel with one or more of a memory 405 which may optionally include or be interfaced with one or more of program storage 410 and/or data storage 415, an input processor or interface 425 for receiving inputs from one or more sensors, and/or an output processor or interface 420 for communicating instructions or signals to one or more actuators. A controller may be interfaced with and/or communicate with a user interface 470 for issuing instructions to the controller or apparatus and/or receiving and/or displaying information from the controller or apparatus; an external storage device 417 such as, for example, a disk drive or flash memory device; and/or a network interface 475 for use in, for example, interfacing the apparatus to other laboratory instruments or reporting operations to and/or receiving instructions from a computer. A controller may be configured and/or programmed to produce a sequence of signals and/or outputs and/or to control one or more actuators in a predetermined sequence and/or in response to user inputs and/or inputs from sensors or other devices or sources. A desired sequence of movements and/or operations may be implemented in whole or part via a program stored in a memory and executed by a processor, and/or may be implemented in whole or part by suitably configured hardware, such as, for example, the opening or closing of a switch by contact with a moving component or under direct user control. In various embodiments, one or more controllers, sensors, and/or actuators may be employed to execute and/or control the execution of any one or more steps of any of the methods disclosed herein.

In some embodiments, there may be provided an actuator, which may be controlled by controller optionally in response to a signal from a sensor, for adjusting the position of a cap gripper and/or cap gripper assembly relative to a rack holder, spinner assembly, or other component. In some embodiments, for example, a cap gripper assembly is gradually displaced away from a spinner assembly so as to accommodate the displacement of a screw cap relative to a vial as the vial is rotated relative to the cap. In some embodiments it will be found useful to displace a cap gripper assembly away from a spinner assembly under control of a controller in response to a sensor of the pressure between vials and spinners, and/or at a rate slightly slower than the rate of movement of the cap on the threads, so as to maintain a desired pressure between the vials and the spinners. In some embodiments this displacement of the cap due to rotation on the threads may be accommodated by allowing the cap to displace against friction or against a cap biasing component or otherwise within the cap gripper. In some embodiments this displacement is adequately accommodated by the ability of the vial to displace as permitted by the resilience and tapered geometry of the spinners. In some embodiments it will be found useful to displace the cap gripper assembly toward a spinner assembly after gripping the caps in the cap gripper assembly, which will further compress the vials against the spinners to account for any variance on the bottom of the vials and help prevent slippage.

In some embodiments there may be provided one or more locking or restraining mechanisms for restraining vials against longitudinal movement, such as, for example, hydraulically or pneumatically actuated bladders or brakes or mechanical restraints or brakes, which may be included as part of a vial rack or as a component of the apparatus or any component thereof.

Each of the components, apparatus, and embodiments disclosed herein may usefully be employed as separate devices. Many useful combinations of the components, apparatus, and embodiments disclosed herein can be made, such as, for example, a combined apparatus, of which various embodiments are illustrated in FIGS. 12-17, for capping or de-capping a plurality of vials 115, each vial having a cap accepting portion 135 for accepting a cap applied and removed by a rotational movement, the vials being rotatably disposed each in a compartment 130 of a vial rack 100, each compartment having associated therewith at least one opening 105 extending from the compartment to the exterior of the rack, the apparatus including: a rack holder stage comprising a rack holder 150 for receiving the vial rack; a vial spinner stage 300 comprising a plurality of spinners 305, each spinner disposed to align with an opening of the vial rack; a spinner drive 315 for imparting rotation to the spinners; a cap gripper stage 200 comprising a plurality of cap grippers 205, each cap gripper enclosing all or part of a cap receiving space 225; a gripper actuator 212 for selectably actuating the grippers to one of a cap gripping configuration or a cap release configuration; a vial rack positioning actuator 140 for selectably positioning the vial rack holder and vial spinner stage relative one to the other in one of (a) an engaged position as illustrated in FIG. 15 wherein the vial rack is engaged with the vial spinner stage to position each of the vials in contact with at least one spinner, or (b) a disengaged position as illustrated in FIG. 14 wherein the vial rack is disengaged from the vial spinner stage to allow loading or unloading of the vial rack from the apparatus; a cap gripper stage positioning actuator 250 for selectably positioning the cap gripper stage and the rack holder relative one to the other in one of (a) an operating configuration as illustrated in FIG. 15 wherein the cap accepting portion of each of the vials is positioned in the cap receiving space of a gripper, or (b) a displaced configuration as illustrated in FIGS. 14 and 16 wherein the cap gripper stage and the rack holder stage are displaced one from the other relative to the operating configuration. It will be apparent that the positioning of components relative one to another or to a support can be accomplished in many equivalent ways, and that, for example, positioning a first component relative to a second component which is positioned relative to a third component is equivalent to positioning the first component relative to the third component. Likewise, it will be apparent that positioning a first component relative to a second component is the equivalent of positioning the second component relative to the first.

In some embodiments of a combined apparatus as illustrated schematically in FIGS. 12-16, there may further be provided one or more supports, such as, for example, support columns 145, on which the vial spinner assembly, cap gripper assembly, and rack holder are disposed in a fixed alignment one with the other. In some embodiments of a combined apparatus as illustrated schematically in FIGS. 12-16, there may be provided one or more sensors for sensing a position of any component or work piece, such as, for example, a vial rack, a vial, a cap, a spinner stage, a rack holder, a rack holder stage, or a cap gripper stage; a controller configured to control a controllable component of the apparatus such as, for example, a spinner stage positioning actuator, a cap gripper stage positioning actuator, a cap gripper actuator, a spinner drive, a rack clamp, or a rack receiver, which control may be in response to an input such as, for example, a signal from a sensor, a signal from a computer, a signal from another device or apparatus, or an input from a user. In some embodiments of a combined apparatus as illustrated schematically in FIGS. 12-16, there may be provided a user interface, which may be integral with and/or serve as a controller or may be a separate component, may interface with a controller and/or control one or more components of the apparatus directly.

In some embodiments of an apparatus including a component such as a spinner assembly, cap gripper assembly, and/or vial rack holder disposed on a support, there is provided an interface for affixing or associating the component to the support, which may be adapted and configured to accommodate removal of the component and replacement thereof by another component. Thus, for example, in the combined apparatus as illustrated schematically in FIGS. 12-16, an interface may be provided whereby the cap gripper assembly, the spinner assembly, and/or the rack holder may be removed from the support columns and/or from the stages in which they are disposed, and replaced with another cap gripper assembly, spinner assembly, and/or rack holder so as, for example, to accommodate a vial rack or vials in a different size or arrangement. In some embodiments, caps in a cap gripper and/or cap gripper assembly may be replaced or substituted while the cap gripper assembly is removed from the apparatus or within the apparatus. In some embodiments, cap gripper assemblies and/or cap racks and/or vial racks may be barcoded and the apparatus may be equipped with a barcode scanner to ensure that caps are reapplied to the correct vials.

Figure 18:
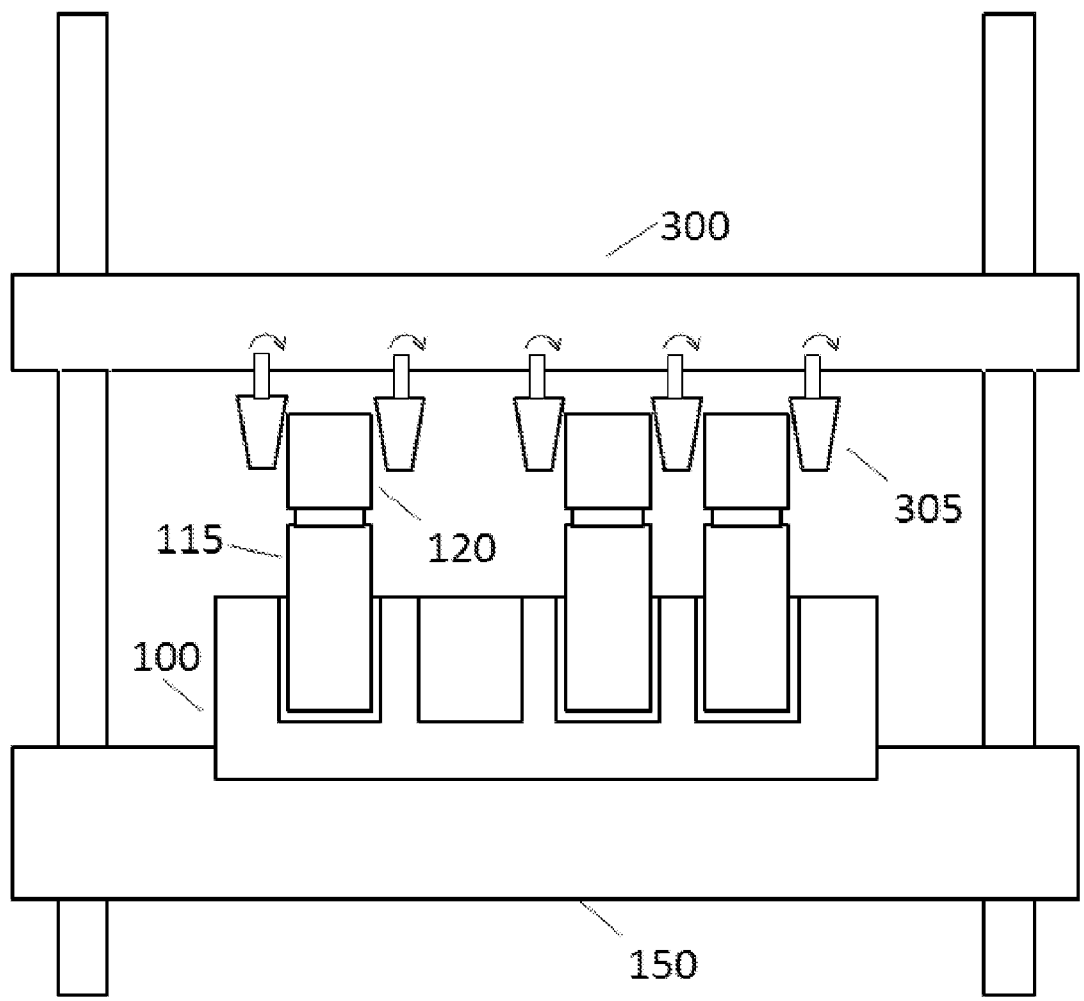
FIG. 18 depicts schematically an alternative embodiment of an apparatus for capping or de-capping a plurality of vials.

An apparatus and/or components thereof and methods as disclosed herein may also be usefully applied as illustrated schematically in FIG. 18 to rotate a plurality of caps 120 relative to vials 115, by contacting each cap with at least one spinner 305 and imparting a rotation to the cap by friction between the spinner and cap, while restraining the vials against rotation. The spinners may be incorporated in a spinner assembly or stage 300 as disclosed herein. In some embodiments, the caps may be disposed in a cap rack having spinner access openings, the cap rack having a construction and geometry similar or identical to that of a vial rack as disclosed herein, but dimensioned to contain caps and permit their rotation within the cap rack. The vials may be disposed in a vial rack, which may be disposed in or on a vial rack holder as disclosed herein. The vials may be restrained against rotation by a vial locking component which may include any device or component operable to restrain a vial from rotation relative to a cap, such as, for example, a gripper assembly disposed and configured to engage the vial bodies and restrain them by friction, or via a pneumatic or hydraulic bladder or mechanical restraint incorporated into the vial rack, or via one or more restraining components that access the vials via openings in the rack. For example, in some embodiments, a spinner assembly may be applied via spinner access openings in the vial rack to impart a rotation force to the vials in one direction, while simultaneously applying another spinner assembly to the caps as illustrated in FIG. 18 to impart an oppositely oriented rotation force to the caps.

Figure 19:
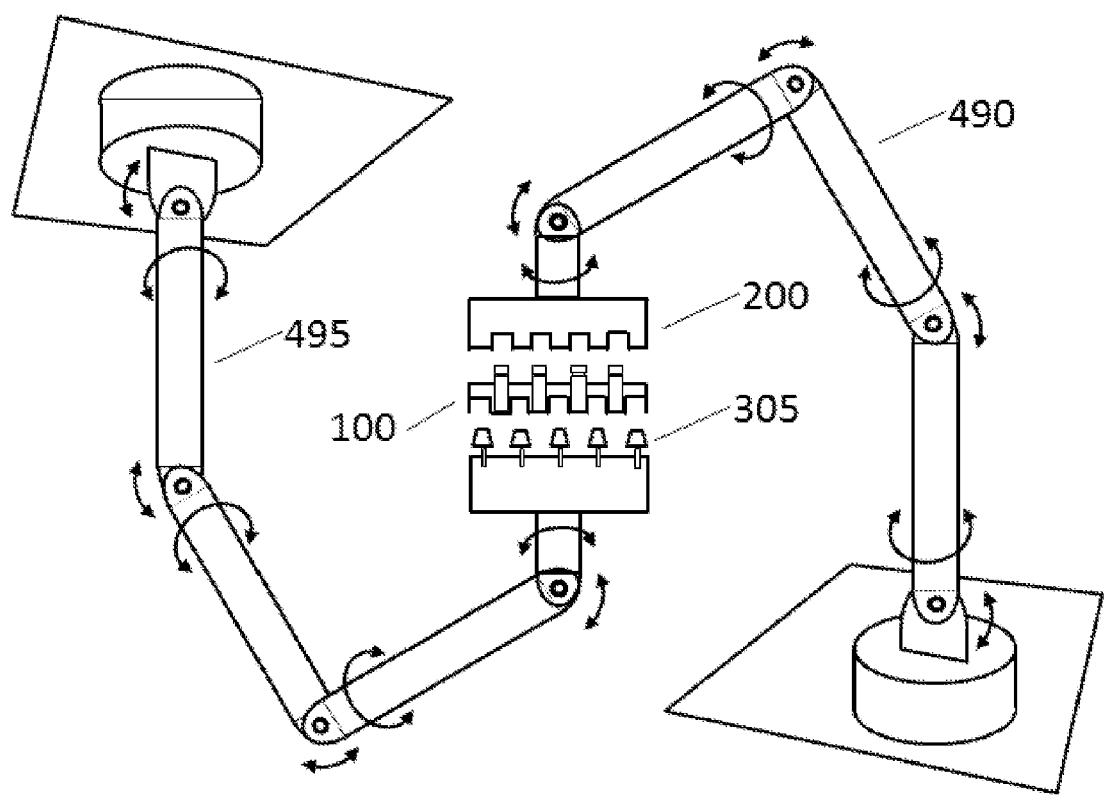
FIG. 19 depicts schematically an embodiment of a cap gripper assembly and spinner assembly each associated with a robotic arm.

In some embodiments, there is provided a system including two or more components such as, for example, one or more spinner assemblies, spinners, cap gripper assemblies, cap grippers, vial rack holders, or vial holders, which are not integrated in a single apparatus but disposed, adapted and configured in any manner operable to function cooperatively for rotating a plurality of caps relative to vials. For example, as illustrated schematically in FIG. 19, a spinner assembly 300, cap gripper assembly 200, or other component may be operatively coupled to a robotic arm 490 495, by which it is positioned relative to a vial rack 100 or other component, and the component controlled to perform an operation such as, for example, rotating vials within a rack or restraining the caps of vials against rotation.

In some embodiments an apparatus may rotates caps and vials simultaneously in opposite directions. In some embodiments cap rotation actuators are used to rotate the caps, and a chuck may be provided between the cap rotation actuators and over each cap to hold the cap in place while it is being rotated. In various embodiments a chuck may be any component, structure, or device operable to grip, restrain, and/or apply a force to a cap. In some embodiments the chuck may be disposed to spin freely with the cap to serve as a holder to prevent caps from being discharged from the machine. In some embodiments a chuck may grip the cap from the outside, the inside, or in any other manner compatible with the caps being used. In some embodiments chucks may be interchanged, providing flexibility in the types of tubes and vials being capped or de-capped. In some embodiments chucks may be disposed in a cap rack.

In some embodiments, there is provided an apparatus for capping or de-capping a plurality of vials adapted to receive rotationally securable and removable caps, the apparatus including means for performing the function of restraining the caps against rotation, and means for performing the function of rotating the vials while the caps are so restrained.

In some embodiments of an apparatus including a spinner assembly, there may be provided one or more positioning actuators for positioning spinners. In some embodiments it may be found useful to provide for the positioning of spinners along their axis of rotation so as to provide a desired degree of contact force between a spinner and a vial. An actuator for positioning a spinner along its axis of rotation may operate passively, such as via a spring or other biasing component for maintaining a desired force or pressure, or may include one or more components such as, for example, motors or solenoids, for providing a desired motion or pressure, which may be under the control of a controller and/or in response to a signal from a sensor. In some embodiments it may be found useful to provide for the positioning of spinners and/or cap grippers in a lateral direction, such as, for example, to align the spinners and/or cap grippers with an arrangement of vials in a vial rack and/or to provide for the accommodation of more than one size or arrangement of vials. Such alignment may be provided via one or more actuators adapted and configured to position one or more spinners and/or cap grippers in a desired position within a spinner assembly or cap gripper assembly, which may be under the control of a controller in response to a signal from a sensor or an instruction from a user.

Also disclosed herein is a method of using an apparatus including a spinner assembly, the method including contacting each of a plurality of vials with at least one spinner of the spinner assembly, and imparting a rotation to the vials through friction by rotating the spinners in contact with the vials. In some embodiments, the vials are disposed in a rack and the method includes positioning the spinner assembly relative to the rack in an alignment and position whereby at least one spinner is in contact with each vial and the axes of rotation of the spinners and the axes of rotation of the vials are approximately parallel. In some embodiments the apparatus includes a rack holder and the method further includes operating the rack holder and/or an actuator associated therewith to dispose the rack in an engaged position in relation to the spinner assembly wherein at least one spinner is in contact with each vial disposed in the rack. In some embodiments, the apparatus includes a cap gripper assembly, and the method further includes operating the cap gripper assembly to restrain a vial cap against rotation.

In an exemplary embodiment consistent with the disclosure hereof as illustrated in FIGS. 14, 15, and 16, there is provided a method of using an apparatus having a spinner assembly or stage 300 including a plurality of spinners 305, a rack holder 150, and a cap gripper assembly 200, the method including: from an initial configuration such as, for example, that illustrated schematically in FIG. 14 in which a vial rack 100 containing a plurality of vials 115 having caps 120 is not engaged with a spinner assembly or cap gripper assembly, engaging, such as, for example, shown schematically in FIG. 15, the spinner assembly with the vials whereby at least one spinner is in contact with each vial, and engaging the cap gripper with the caps whereby the cap of each vial is present in a cap receiving space 225 of the cap gripper assembly; then operating the cap grippers of the cap gripper assembly to restrain the caps from rotation, while rotating the spinners in contact with the vials to impart a rotation to the vials. In some embodiments, the method may further include, as in the example illustrated in FIG. 16, displacing the cap gripper assembly away from the vials while operating the cap grippers to grip the caps, thereby removing the caps from the vials. In some embodiments the method may further include disengaging the rack holder, rack and/or vials from the spinner assembly. In some embodiments the method may further include operating the rack holder to the loading/unloading position and/or removing the rack and vials from the rack holder. In some embodiments the method may include loading a rack containing a plurality of vials in the rack holder while the rack holder is in a loading/unloading position, and/or operating the rack holder to the retracted position, prior to or in the course of engaging the spinner assembly with the vials.

In an exemplary embodiment consistent with the disclosure hereof as illustrated in FIGS. 14, 15, and 16, there is provided a method of using an apparatus having a spinner assembly or stage 300 including a plurality of spinners 305, a rack holder 150, and a cap gripper assembly 200 including a plurality of cap grippers, the method including: from an initial configuration as illustrated schematically in FIG. 16 wherein a plurality of caps are present in the cap receiving spaces of the cap gripper assembly, and a rack containing un-capped vials is present in the rack holder and at least one spinner is positioned in contact with each vial, displacing the cap gripper assembly toward the rack holder, rack, and/or vials to position the caps in contact with the cap receiving portions of the vials, and rotating the spinners to impart by friction between the spinners and vials a rotation to the vials relative to the caps, while or after operating the cap grippers to a gripping configuration to restrain the caps against rotation.

In an exemplary embodiment consistent with the disclosure hereof, there is provided a method of using an apparatus having a spinner assembly or stage including a plurality of spinners, a rack holder, and a cap gripper assembly including a plurality of cap grippers, the method including: placing in the rack holder a vial rack containing a plurality of vials provided with caps removable by a rotational movement relative to the vials; positioning the vial rack and vial spinner assembly relative to each other whereby each vial is contacted by a spinner; positioning the cap gripper assembly and caps relative one to another whereby each cap is positioned in the cap receiving space of a cap gripper; actuating the grippers to grip the caps; and actuating the spinners to rotate against the vials and thereby impart a rotation to the vials.

Also disclosed herein is a method, which may be used for tightening or loosening rotationally securable caps in relation to a plurality of vials disposed in a rack, the method including rotating the vials in the rack while restraining the caps against rotation. In some embodiments, rotating a vial may include positioning at least one actuator in contact with each vial and by a motion of the actuator imparting a torsional force on the vial by friction. By way of example, in some such embodiments, the actuator may be or include a spinner and moving the actuator may include rotating the spinner in frictional contact with the vial; in some embodiments, the actuator may include a belt and moving the actuator may include translating the belt in frictional contact with the vial. In some embodiments, rotating the vials may include positioning an actuator in contact with two or more vials and by a motion of the actuator simultaneously imparting torsional forces to the two or more vials by friction. In some embodiments, rotating the vials may include positioning at least two actuators in contact with at least one vial and by simultaneous motions of the actuators imparting torsional forces to the vial by friction. In some embodiments, the contact of the actuator with the vial may be exclusively a frictional contact, or substantially a frictional contact. In some embodiments, the surface of the actuator in contact with the vial may be a substantially smooth surface. In some embodiments, the region of contact of the actuator with the vial is entirely aligned on a cylindrical or circumferential exterior surface of the vial. In some embodiments, a torsional force is imparted to a vial by friction alone, or substantially by friction, and/or without applying to the vial a force having a component normal to a non-circumferential surface of the vial. In some embodiments, positioning an actuator in contact with a vial does not include or entail, and/or a vial is not rotated by, engaging a key such as a wrench, blade, or driver with torsion-transmitting feature of the vial such as, for example, a tooth, socket, keyway, indentation, protrusion, or lug. In some embodiments, a plurality of vials is rotated wherein each vial has a substantially circular cross-section in any plane perpendicular to its axis of rotation. In some embodiments, a plurality of vials is rotated and the vials are generic glass or plastic vials. In some embodiments, a plurality of vials is rotated and each vial comprises a container or vial body portion and a cap accepting portion and the container or vial body portion is generally cylindrical or cylindrical with a rounded base.

Also disclosed herein is a method, which may be used for tightening or loosening rotationally securable caps in relation to a plurality of vials disposed in a rack, the method including rotating the caps while restraining the vials against rotation. In some embodiments, the caps may be disposed in a cap rack, which may be adapted and configured to hold caps in a desired orientation and/or allow rotation of the caps therein. In some embodiments, rotating a cap may include positioning at least one actuator in contact with each cap and by a motion of the actuator imparting a torsional force on the cap by friction. By way of example, in some such embodiments, the actuator may be or include a spinner and moving the actuator may include rotating the spinner in frictional contact with the cap; in some embodiments, the actuator may include a belt and moving the actuator may include translating the belt in frictional contact with the cap. In some embodiments, rotating the caps may include positioning an actuator in contact with two or more caps and by a motion of the actuator simultaneously imparting torsional forces to the two or more caps by friction. In some embodiments, rotating the caps may include positioning at least two actuators in contact with at least one cap and by simultaneous motions of the actuators imparting torsional forces to the cap by friction. In some embodiments, the contact of the actuator with the cap may be exclusively a frictional contact, or substantially a frictional contact. In some embodiments, the surface of the actuator in contact with the cap may be a substantially smooth surface. In some embodiments, the region of contact of the actuator with the cap is entirely aligned on a cylindrical or circumferential surface of the cap. In some embodiments, positioning an actuator in contact with a cap does not include or entail, and/or a cap is not rotated by, engaging a key such as a wrench, blade, or driver with torsion-transmitting feature of the cap such as, for example, a tooth, socket, keyway, indentation, protrusion, or lug. In some embodiments, a torsional force is imparted to a cap by friction alone, or substantially by friction, and/or without applying to the cap a force having a component normal to a non-circumferential surface of the cap. In some embodiments, a plurality of caps is rotated wherein each cap has a substantially circular cross-section in any plane perpendicular to its axis of rotation. In some embodiments, a plurality of caps is rotated and the caps are generic metal or plastic caps. In some embodiments, a plurality of caps is rotated and each cap is generally cylindrical or cylindrical with a rounded or recessed top.

In some embodiments, a method of tightening or loosening rotationally securable caps in relation to a plurality of vials disposed in a rack includes disengaging the caps from the vials after the caps have been rotated. In some embodiments, a method of tightening or securing rotationally securable caps in relation to a plurality of vials disposed in a rack includes, prior to rotating the vials, positioning the caps in rotationally securable engagement with the vials, that is, positioning the caps in contact with the cap accepting portions of the corresponding vials in a position whereby rotation of the vials will result in tightening or securing the caps.

The methods disclosed herein may be performed in whole or in part in any operable manner, such as, for example, by controlling and/or positioning components by hand, by the use of tools or devices, robotically, under the control of a computer or controller, or in any other automated, non-automated, or partially automated manner. In some embodiments such as the exemplary embodiment illustrated schematically in FIG. 17, an apparatus may include a control system for operating the apparatus to carry out all or any part of a method as disclosed herein, which control system may include one or more sensors, actuators, controllers, and/or interfaces dispose, adapted, and configured to operate any one or more components of the apparatus to perform an operation or method step in a sequence that may be determined in whole or part by one or more inputs from one or more sensors, user interfaces, computers, other instruments, or other sources, processed according to a software program, user directions or controls, hardware logic, or otherwise, and producing one or more outputs to one or more actuators. In an embodiment, an apparatus including a spinner assembly, rack holder, and cap gripper assembly further includes a control system including a microcontroller, interfaced to a user interface and sensors and actuators, and programmed to perform a capping and/or de-capping operation according to the methods disclosed herein.

CONCLUDING MATTER

For clarity and to ensure completeness, certain of the aspects and/or embodiments disclosed herein may be overlapping in scope, described repetitively, or represent recitals of the same or equivalent elements or combinations expressed in alternative language. It will be apparent that the choice of particular phraseology and/or of particular aspects or elements to assert as claims involves many complex technical and legal considerations, and no inference should be drawn that alternative descriptions of a particular element or combination in this written description necessarily do or do not encompass different subject matter; except where context otherwise requires, each described aspect or element should be interpreted according to its own description.

It is intended that this specification be interpreted in accordance with the normal principles of English grammar and that words and phrases be given their ordinary English meaning as understood by persons of skill in the pertinent arts except as otherwise explicitly stated. If a word, term, or phrase is intended to be further characterized, specified, or narrowed in some way, then additional adjectives, modifiers, or descriptive text have been included in accordance with the normal principles of English grammar. It is intended that the meanings of words, terms, or phrases should not be modified or characterized in a manner differing from their ordinary English meaning as understood by persons of skill in the relevant arts except on the basis of adjectives, modifiers, or descriptive text that is explicitly present.

Except as otherwise explicitly stated, terms used in this specification, including terms used in the claims and drawings, are intended as "open" terms. That is, for example, the words "including" and "comprising" should be interpreted to mean "including but not limited to," the word "having" should be interpreted to mean "having at least," the word "includes" should be interpreted to mean "includes but is not limited to," the phrases "for example" or "including by way of example" should be interpreted as signifying that the example(s) given are non-exhaustive and other examples could be given, and other similar words and phrases should be given similar non-exclusive meanings.

In the written description and appended claims, the indefinite articles "a" and/or "an" are intended to mean "at least one" or "one or more" except where expressly stated otherwise or where the enabling disclosure requires otherwise. The word "or" as used herein is intended to mean "and/or", except where it is expressly accompanied by the word "either", as in "either A or B". Applicants are aware of the provisions of 35 U.S.C. §112, ¶6. The use of the words "function," "means" or "step" in the written description, drawings, or claims herein is not intended to invoke the provisions of 35 U.S.C. §112, ¶6, to define the invention. To the contrary, if the provisions of 35 U.S.C. §112, ¶6 are sought to be invoked, the claims will expressly include one of the exact phrases "means for performing the function of" or "step for performing the function of". Moreover, even if the provisions of 35 U.S.C. §112, ¶6 are explicitly invoked to define a claimed invention, it is intended that the claims not be limited only to the specific structure, material or acts that are described in the preferred embodiments, but in addition, extend to any and all structures, materials or acts that perform the claimed function as described in alternative embodiments or forms of the invention, or that are well known present or later-developed equivalent structures, material or acts for performing the claimed function.

Any of the methods of the present disclosure may be implemented in whole or part in hardware, software, or both, or by a computer program, and may be carried out using any of the disclosed devices or apparatus according to any aspect or embodiment of the present invention, or in any other operable manner.

In the foregoing description, various details, specific aspects, embodiments, and examples have been described in order to illustrate and explain the subject matter, to provide a thorough understanding of the various aspects, to enable persons skilled in the pertinent arts to practice the described subject matter, and to disclose the best mode of doing so known to applicants. These details, specific aspects, embodiments, and examples are not intended to be limiting; rather, it will be apparent to persons of skill in the relevant arts that, based upon the teachings herein, various changes, substitutions, modifications, rearrangements, may be made and various aspects, components, or steps may be omitted or added, without departing from the subject matter described herein and its broader aspects. Except as otherwise expressly stated or where aspects or features are inherently mutually exclusive, aspects and features of any embodiment described herein may be combined with aspects and features of any one or more other embodiments. The appended claims are intended to encompass within their scope any and all changes, substitutions, modifications, rearrangements, combinations of aspects or features, additions, and omissions that are within the spirit and scope of the subject matter as described herein and/or within the knowledge of a person of skill in the art. The scope of the invention is defined by the claims, and is not limited by or to the particular embodiments or aspects chosen for detailed exposition in the foregoing description, but rather extends to all embodiments or aspects as defined by the claims, as well as any equivalents of such embodiments or aspects, whether currently known or developed in the future.

So as to reduce the complexity and length of the detailed description, and to provide background in certain areas of technology, each of the materials identified in the "REFERENCES" section below is expressly incorporated by reference. Applicants believe that the subject matter incorporated is "non-essential" in accordance with 37 CFR 1.57, because it is referred to for purposes of indicating the background of the invention or illustrating the state of the art. However, if the Examiner concludes that any of the incorporated material constitutes "essential material" within the meaning of 37 CFR 1.57(c)(1)-(3), applicants will amend the specification to expressly recite the essential material that is incorporated by reference as allowed by the applicable rules.

REFERENCES

Bisset B., Practical Pharmaceutical laboratory automation (2003), CRC Press, Boca Raton.
Cork D. and Sugawara, T., Laboratory Automation in the Chemical Industries (2002) Marcel Dekker, New York.
Nicolao, H., Laboratory Automation (2011), Crypt Publishing
Niku, S., Introduction to Robotics: analysis Control, Applications (2010), Wiley.

We claim:

1. An apparatus for rotating a plurality of vials, comprising:
a plurality of spinners disposed in a spinner assembly, each spinner positioned to contact at least one vial while rotating and thereby impart a rotation to the vial substantially by friction between the spinner and the vial; and
one or more spinner actuators for rotating the spinners;
wherein the vials are disposed in a vial rack having spinner access openings therein, and the spinners are positioned in an arrangement alignable with the spinner access openings.

2. The apparatus of claim 1, further comprising a rack holder.

3. The apparatus of claim 1, further comprising a positioning actuator for positioning the spinner assembly and rack holder relative one to another to engage or disengage the spinners from the vials.

4. The apparatus of claim 1, wherein the vials are adapted to accept caps, the apparatus further comprising: a plurality of cap grippers disposed in a cap gripper assembly in an arrangement alignable with the cap accepting portions of the vials; and at least one cap gripper actuator for operating the cap grippers to grip or release a cap.

5. The apparatus of claim 4, further comprising a positioning actuator for positioning the cap gripper assembly relative to the vials to engage the cap grippers with caps affixed to the vials or position caps gripped in the cap grippers in contact with the cap accepting portions of the vials.

6. The apparatus of claim 1, wherein a spinner comprises a tapered rotor.

7. The apparatus of claim 1, wherein a spinner comprises a resilient material.

8. The apparatus of claim 1, wherein the impartation of rotation to the vial by the spinner is keyless.

9. The apparatus of claim 1, wherein at least one spinner is positioned to contact simultaneously a plurality of vials while rotating and impart rotation to each of the plurality of vials.

10. The apparatus of claim 1, wherein a plurality of spinners are positioned to contact simultaneously a single vial and each impart a rotation to the vial.

11. A method of using the apparatus of claim 1 for decapping a plurality of vials fitted with rotatably removable caps wherein the vials are disposed in a vial rack having spinner access openings therein, the method comprising:
restraining the cap of each vial against rotation;
contacting a vial with at least one spinner via a spinner access opening; and
rotating the at least one spinner in contact with the vial to impart a rotation to the vial substantially by friction between the spinner and the vial.

12. An apparatus for rotating a plurality of vials, comprising:
a plurality of spinners disposed in a spinner assembly, each spinner positioned to contact at least one vial while rotating and thereby impart a rotation to the vial substantially by friction between the spinner and the vial; and
one or more spinner actuators for rotating the spinners;
wherein at least one spinner is positioned to contact simultaneously a plurality of vials while rotating and impart rotation to each of the plurality of vials.

* * * * *